United States Patent
Saleem

(10) Patent No.: US 11,293,845 B2
(45) Date of Patent: Apr. 5, 2022

(54) NON-DESTRUCTIVE ANCHOR BOLT PULL OUT LOAD CAPACITY TESTING SYSTEM

(71) Applicant: Imam Abdulrahman Bin Faisal University, Dammam (SA)

(72) Inventor: Muhammad Saleem, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 17/197,178

(22) Filed: Mar. 10, 2021

(65) Prior Publication Data

US 2021/0190654 A1  Jun. 24, 2021

Related U.S. Application Data

(63) Continuation of application No. 16/198,078, filed on Nov. 21, 2018, now Pat. No. 10,969,315.
(Continued)

(51) Int. Cl.
*G01N 3/14* (2006.01)
*G01N 33/38* (2006.01)
(Continued)

(52) U.S. Cl.
CPC ............... *G01N 3/14* (2013.01); *G01M 1/00* (2013.01); *G01N 29/07* (2013.01); *G01N 33/383* (2013.01);
(Continued)

(58) Field of Classification Search
CPC ......... G01N 3/14; G01N 29/07; G01N 33/383
(Continued)

(56) References Cited

U.S. PATENT DOCUMENTS

| 4,942,668 A | 7/1990 | Franklin |
| 6,655,213 B1 * | 12/2003 | Reinhardt ............. G01N 29/07 73/597 |

(Continued)

FOREIGN PATENT DOCUMENTS

| CN | 102539262 A | 7/2012 |
| GB | 1 549 842 | 8/1979 |

OTHER PUBLICATIONS

Jobli, et al. ; The role of ultrasonic velocity and Schmidt hammer hardness—The simple and economical non-destructive test for the evaluation of mechanical properties of weathered granite ; International Conference on Applied Physics and Engineering ; AIP Publishing ; 9 Pages.

(Continued)

*Primary Examiner* — Ricky Go
(74) *Attorney, Agent, or Firm* — Oblon, McClelland, Maier & Neustadt, L.L.P.

(57) ABSTRACT

A tester for evaluating pullout load capacity and bond quality of anchor bolts embedded in concrete includes a Schmidt hammer for measuring a rebound number and an ultrasonic pulse velocity tester for measuring the transit time of a pulse transmitted through concrete surrounding an anchor bolt. The rebound number and the transit time are combined and matched against a database record which identifies the pullout load capacity and the bond quality. The transit time is matched to thresholds of transit times associated with porosity, internal cracking, air voids, and water pockets located around the embedded anchor bolt. The Schmidt hammer is further modified by the incorporation of a digital level for measuring the vertical and horizontal angles of inclination of the plunger with the concrete surface, a guide tube for supporting the plunger, and by using (Continued)

a convex plunger tip for improved registration with anchor bolt head.

16 Claims, 24 Drawing Sheets

Related U.S. Application Data

(60) Provisional application No. 62/597,801, filed on Dec. 12, 2017.

(51) Int. Cl.
  G01N 29/07 (2006.01)
  G01M 1/00 (2006.01)
  G01N 29/34 (2006.01)

(52) U.S. Cl.
  CPC .............. *G01N 29/343* (2013.01); *G01N 2203/0039* (2013.01); *G01N 2203/0083* (2013.01); *G01N 2291/011* (2013.01); *G01N 2291/0232* (2013.01); *G01N 2291/2691* (2013.01)

(58) Field of Classification Search
  USPC .......................................... 702/43
  See application file for complete search history.

(56) References Cited

U.S. PATENT DOCUMENTS

| | | |
|---|---|---|
| 8,261,620 B2 | 9/2012 | Brandestini |
| 9,127,998 B1 | 9/2015 | Guldiken |
| 2010/0307258 A1 | 12/2010 | Brandestini |
| 2011/0167754 A1 | 7/2011 | Dubon |
| 2011/0179873 A1 | 7/2011 | Schubert |
| 2015/0160167 A1 | 6/2015 | Kawasaki |
| 2015/0309007 A1 | 10/2015 | Bellotti |
| 2016/0282230 A1 | 9/2016 | Poser |
| 2017/0102304 A1 | 4/2017 | Saleem |

OTHER PUBLICATIONS

Mahmoudipour ; Statistical Case Study On Schmidt Hammer, Ultrasonic and Core Compression Strength Tests' Results Performed on Cores Obtained From Behbahan Cement Factory in Iran ; Geotechnical Department, SANO Consulting Engineers, No. 11 ; 8 Pages.

Mohammed, et al. ; Evaluation of rubbercrete based on ultrasonic pulse velocity and rebound hammer tests ; ScienceDirect; Construction and Building Materials, vol. 25, Issue 3 ; pp. 1388-1397 ; Mar. 2011 ; Abstract Only ; 2 Pages.

FPrimeC ; How to Estimate Strength of Concrete Using NDT Methods? ; May 24, 2018 ; http://www.fprimec.com/how-to-estimate-strength-of-concrete-using-ndt-methods/ ; 6 Pages.

Shariati, et al. ; Assessing the strength of reinforced concrete structures through Ultrasonic Pulse Velocity and Schmidt Rebound Hammer tests ; Scientific Research and Essays, vol. 6 (1) ; pp. 213-220 ; Apr. 1, 2011 ; 9 Pages.

Humboldt ; Ultrasonic Pulse Velocity Tester; https://www.humboldtmfg.com/ultrasonic-pulse-velocity-tester.html ; 3 Pages.

Cemex USA ; Proper use of the Rebound Hammer, Updated to reflect the changes to ASTM C805 ; Technical Bulletin 2.1 ; 6 Pages.

Humboldt ; Humboldt Concrete Rubber Hammer; https://www.humboldtmfg.com/humboldt-concrete-reboundhammer.html ; 5 Pages.

Proceq ; Schmidt rebound hammers for concrete strength and rock testing ; https://www.proceq.com/compare/schmidt-hammers/; 8 Pages.

* cited by examiner

NON-DESTRUCTIVE ANCHOR BOLT PULL OUT LOAD CAPACITY TESTING SYSTEM

CROSS-REFERENCE TO RELATED APPLICATIONS

The present application is a continuation of application Ser. No. 16/198,078, allowed, having a filing date of Nov. 21, 2018 which claims priority to Provisional Application No. 62/597,801 entitled "Combined Use Of Ultrasonic Pulse Velocity Test and Schmidt Hammer Test For Increased Judgment Accuracy In Determining The Pullout Strength Of Anchor Bolts" filed on Dec. 12, 2017, the entire contents of which is incorporated herein in its entirety, and is related to Non-Provisional application Ser. No. 14/880,185, now publication U.S. 2017/0102304A1, having common inventorship with the present application and filed in the U.S. Patent and Trademark Office on Oct. 9, 2015, the entire contents of which are incorporated herein by reference.

BACKGROUND

Technical Field

The present disclosure is directed to a Schmidt Hammer device, method and system for testing the pullout load capacity of anchor bolts. An ultrasonic pulse velocity test is combined with a Schmidt Hammer rebound number to determine faulty bolt installation or bolt seating.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Steel bolts are used in the construction industry for a large variety of applications that range from attaching permanent installations to temporary fixtures. Destructive testing techniques are known which estimate the pullout load capacity of these bolts.

In construction technology, destructive pullout testing generally establishes the holding force of steel bolt anchors and fixings in most construction materials, such as concrete. Conventional pullout testing of anchor bolts or bars requires applying a specific tensile load to an anchor bolt or bar in order to measure whether the anchor bolt or bar remains seated for a period of time. Deformation of the anchor can also be measured to understand the relationship between force and displacement during testing.

However, non-destructive techniques are needed to avoid weakening the bolt or the bolt seat.

Non-destructive testing is a wide group of analysis techniques used in science and industry to evaluate the properties of a material, component or system without causing damage. NDT is used extensively in the construction industry to evaluate the condition of existing structures and provides engineers with a tool to estimate the strength of materials and components without damaging them.

The Schmidt hammer was developed in 1948 by Swiss engineer Ernst Schmidt and is a portable, cost-effective instrument capable of estimating the elastic properties of hardened concrete. The Schmidt hammer rebound test is a practical, non-destructive testing method that has been used worldwide as an index test for estimating the compressive strength of concrete.

The Schmidt hammer consists of a plunger rod, an internal spring loaded steel hammer and a latching mechanism. When the extended plunger rod distal end is pushed against a hard surface, the spring connecting the hammer is stretched and when pushed to an internal limit, the latch is released causing the energy stored in the stretched spring to propel the hammer against the plunger tip. The hammer strikes the shoulder of the plunger rod and rebounds a certain distance. There is a slide indicator on the outside of the unit that records the distance traveled during the rebound. This indication is known as the rebound number. By pressing the button on the side of the unit, the plunger is then locked in the retracted position and the rebound number (R-number) can be read from the graduated scale. A higher R-number indicates a greater hardness of the concrete surface. (See CEMEX USA-Technical Bulletin. "Proper use of the Rebound Hammer Updated to reflect the changes to ASTM C805", https: www.cemexusa.com/documents/27329108/ 45560536/proper-use-of-the-rebound-hammer.pdf/ 1417ecb8-2a04-1b8a-48aa-853149c76936, incorporated herein by reference in its entirety).

U.S. Pat. No. 8,261,620, incorporated herein by reference in its entirety, describes a conventional Schmidt hammer as shown in FIG. 1. The Schmidt hammer 100 includes a mallet 3 which is propelled by a first spring 8 to travel along guide rod 4 and impact the proximal end 5a of plunger 5 and spring 6. The distal end 5b of plunger 5 transfers the impact force to a structure to be measured. The plunger rebounds from the impact, forcing the mallet 3 to travel towards the proximal end 10 of the Schmidt hammer. Graduations 11 on the circumference of the mallet 3 are measured by a linear potentiometer (not shown) or an optical sensor 12. The distance the mallet travels on the rebound path is called the rebound number. A circuit board 17 includes processing circuitry to calculate the rebound number and cause the rebound number to be displayed on display 18. A two axis accelerometer (not shown) measures the angle of inclination of the Schmidt hammer with the surface of the structure and can make fine adjustments to the rebound value.

US2017/0102304, incorporated herein by reference in its entirety, describes a non-destructive testing procedure which evaluates the pullout load capacity of concrete anchor bolts by relating their pullout load capacity to the Schmidt hammer rebound number. Defects related to anchor bolt installation were identified and an accurate estimation of the reduction in pullout load capacity owing to the defects was determined using a non-destructive testing procedure. The bond strength of the bolt was influenced by its diameter, its embedment length, alignment and the concrete strength. In US2017/0102304, the embedment depth and concrete strength was kept constant and only the variation in the bolt diameter was investigated.

Saleem et al. ("Study to detect bond degradation in reinforced concrete beams using ultrasonic pulse velocity test method", Structural Engineering and Mechanics, July, 2017), incorporated herein by reference in its entirety, described a ultrasonic pulse velocity test relating variation in pulse velocity to bond quality of reinforced concrete beams. Five identical beams embedded in concrete were subjected to incremental loading increases until failure was detected. It was found that the ultrasonic wave velocity decreased as loading increased. This reduction in wave velocity was attributed to the initiation, development and internal cracking in the concrete surrounding the beam. The procedure was employed to identify zones of poor bonding along the length of the beam.

Destructive evaluation of the anchor bolts was conducted in which the response of concrete anchors subjected to various types of loading under stressed and non-stressed conditions was determined. Results related the deformational behavior of the anchor bolts with their design details in order to refine the dynamic response of anchor bolts. (See Eligehausen et al. "Behavior of Post-Installed Anchors Tested By Stepwise Increasing Cyclic Load Protocols", ACI Structural Journal, Vol 113, Pt. 5, Pg. 997-1008, 2016. Doi: 10.14359/51689023, Hoehler et al. "Behavior and testing of anchors in simulated seismic cracks" ACI Structural Journal, Vol 105, Pt. 3, Pg. 348-357, 2008, Hoehler et al. "Behavior of anchors in cracked concrete under tension cycling at near-ultimate loads", ACI Structural Journal, Vol 105, Pt. 5, Pg. 601-608, 2008, Guillet "Behavior of metal anchors under combined tension and shear cycling loads", ACI Structural Journal, Vol 108, Pt. 3, Pg. 315-323, 2011, Jie et al. "Experimental Investigation on the bond of reinforcing bars in high performance concrete under cyclic loading", Materials and Structures, Vol 40, Pt. 3, Pg. 1027-1044. DOI: 10.1617/s11527-006-9201-1, and Saleem and Nasir "Bond evaluation of steel bolts for concrete subjected to impact loading", Materials and Structures, Vol 49, Pt. 9, Pg. 3635-3646, 2016. DOI 10.1617/s11527-015-0745-9, Saleem, M. and Tsubaki, T. "Multi-layer model for pullout behavior of post-installed anchor", Proc. FRAMCOS-7, Fracture Mechanics of Concrete Structures, AEDIFICA-TIO publishers, Germany, Vol. II, Pg. 823-830, 2010, Saleem, M. "Cyclic Pullout Push-In Shear-Lag Model for Post-installed Anchor-Infill Assembly", Arabian Journal of Science and Engineering, Vol. 39, No. 12, Pg. 8537-8547, 2014. DOI 10.1007/s13369-014-1423-x, each incorporated herein by reference in its entirety.

Impact energy imparted by the Schmidt hammer has been correlated with the strength of rock specimens. (See Torabi, S. R., Ataei, M. & Javanshir, M. "Application of Schmidt rebound number for estimating rock strength under specific geological conditions" Journal of Mining & Environment, Vol. 1, No. 2, Pg. 1-8, 2010, Cargill, J. S. & Shakoor, A. "Evaluation of empirical methods for measuring the uniaxial compressive strength of rock" International Journal of Rock Mechanics, Mineral Science & Geomechanics, Vol. 27, Pg. 495-503, 1990, each incorporated herein by reference in its entirety).

The angle of impact, and surface properties of concrete has been correlated with the effect on the rebound number. The destructive test incorporated the design parameters of concrete. (See Jen-Chei, L., Mou-Lin, S., & Chang-Huan, Kou. "Estimating the Strength of Concrete Using Surface Rebound Value and Design Parameters of Concrete Material" Tamkang Journal of Science and Engineering, Vol. 12, No. 1, Pg. 1-7, 2009, Katalin, S. "Rebound surface hardness and related properties of concrete", PhD Thesis, Budapest University of Technology and Economics, Department of Construction Materials and Engineering Geology, 2013, Brozovsky, J., & Zach, J. "Influence of Surface Preparation Method on the Concrete Rebound Number obtained from Impact Hammer Test" 5th Pan American Conference for Non Destructive Testing, Cancun, Mexico, Pg. 234-239, 2011.

An ultrasonic pulse velocity test was used to investigate the performance of buildings and bridges. The effects of rapid-hardening cement, concrete aggregate type, concrete size, the age of concrete, and its workability were related. Results showed that UPV testing is a useful tool for non-destructive testing of the properties of concrete. (See Mutlib, N. K., Baharom, S. B., El-Shafie, A. and Nuawi, M. Z. "Ultrasonic health monitoring in structural engineering: buildings and bridges", Structural Control and Health Monitoring, Vol. 23, Pg. 409-422, 2016, Mandal, T., Tinjum, J. M. and Edil, T. B. "Non-destructive testing of cementitiously stabilized materials using ultra-sonic pulse velocity test", Transportation Geotechnics, Vol. 6, Pg. 97-107, 2016, Umais, K., Al-Osta, M. A. and Ibrahim, A. "Modeling shear behavior of reinforced concrete beams strengthened with externally bonded CFRP sheets", Structural Engineering and Mechanics, An Int'l Journal, Vol. 61, No. 1, 2017, each incorporated herein by reference in its entirety).

Similarly, the effects of additives such as ground granulated blast furnace slag (GGBFS) and chloride intrusions have been related to the response of ultrasonic pulse velocity. (See Qasrawi, H. Y. and Marie, I. A. "The use of USPV to anticipate failure in concrete under compression", Cement Concrete Research, Vol. 33, No. 12, Pg. 2017-2021, 2013, and Zongping, C., Jinjun, X., Liang, Y. and Yisheng, S. "Bond behaviors of shape steel embedded in recycled aggregate concrete and recycled aggregate concrete filled in steel tubes", Structural Engineering and Mechanics, An Int'l Journal, Vol. 17, No. 6, 2014, each incorporated herein by reference in its entirety).

Saleem, M. and Nasir, M. "Bond evaluation of steel bolts for concrete subjected to impact loading", Materials and Structures, Vol 49, Pt. 9, Pg. 3635-3646, 2016. DOI 10.1617/s11527-015-0745-9, incorporated herein by reference in its entirety, used an ultrasonic pulse velocity test to investigate the bond of concrete elements and found that ultrasonic pulse velocity can be related to the presence of internal cracking at the interface of concrete and embedded steel.

None of the disclosed references describes a combination of using UPV and the Schmidt hammer rebound number in non-destructive testing of anchor bolts embedded in concrete.

The present disclosure further presents a new design of the Schmidt hammer, which increases accuracy in determining the Schmidt hammer rebound number. Other improvements relate the embedment length to the pullout force. These improvements will aid in ensuring that the anchor bolts embedded in concrete structures exhibit high pullout resistance and long lifetimes so that the structural components secured to concrete substrates or substructures by means of such anchor bolts, will be solidly and reliably affixed or secured to the underlying concrete structures.

SUMMARY

The objective of the present disclosure is to provide non-destructive testing of anchor bolts embedded in concrete using a combination of a Schmidt hammer test with an ultrasonic pulse velocity test to determine a pullout load capacity of the anchor bolt for varying embedment lengths. An improved Schmidt hammer device used in the combined test yields a more accurate Schmidt hammer rebound number. A diagnosis of the factors affecting the pullout load capacity, such as bolt alignment, presence of internal cracking, air voids, water pockets is also determined.

A first embodiment includes a device for determining the pullout load capacity of a bolt disposed in concrete. The device includes a controller including processing circuitry, wherein a Schmidt hammer and an ultrasonic pulse velocity tester are electrically connected to the controller. The Schmidt hammer is configured to impact the bolt during a test event and determine a rebound value for the bolt, which is recorded in a data acquisition system of the Schmidt hammer and transmitted to the controller. The UPV test determines the porosity, internal cracking, air voids, and water pockets of the concrete around the bolt. The readings from the UPV test are sent to the controller, where the controller processing circuitry is configured to combine the Schmidt hammer rebound number and UPV readings to determine an estimated pullout load capacity for the bolt based on the rebound value of the bolt, with a database record relating a predetermined bolt diameter, a predetermined bolt embedment length in the concrete with pullout load capacity, and with values related to the determination of the porosity, internal cracking, air voids, and water pockets around the embedded bolt. Determining the estimated pullout load capacity includes comparing, by the processing circuitry, the recorded rebound number and UPV test values with stored look up record values that associate the rebound number and UPV test values to pullout load capacity so as to estimate a pullout load capacity of the bolt.

Another embodiment includes a non-destructive method for determining a pullout load capacity of a bolt disposed in concrete. The method includes impacting the head of the plunger of a Schmidt hammer on the bolt, recording a rebound value for the bolt via a data acquisition system of the Schmidt hammer and transmitting the hammer rebound value to a controller having circuitry for receiving and processing the rebound value. The method further includes conducting an ultrasonic pulse velocity test in the vicinity of the bolt to estimate values related to the porosity, internal cracking, air voids, and water pockets of the concrete surrounding the bolt, and transmitting the value to the controller. The method includes combining the Schmidt hammer rebound number and UPV test results to determine an estimated pullout load capacity for the bolt based on the rebound value of the bolt, a predetermined bolt diameter, a predetermined bolt embedment length in the concrete, and values related to the determination of the porosity, internal cracking, air voids, and water pockets around the embedded bolt. The determining of the estimated pullout load capacity includes comparing, by controller processing circuitry, the recorded rebound number and UPV test values with stored look up record values that associate the hammer rebound number and UPV test values to pullout load capacity so as to estimate a pullout load capacity of the bolt.

Embodiments further include a non-destructive system for determining a pullout load capacity of a bolt disposed in concrete. The system includes a controller including receiving and processing circuitry. The system also includes a Schmidt hammer electrically connected to the controller processing circuitry. The Schmidt hammer is configured to impact the bolt during a test event and to record a rebound value for the bolt in a data acquisition system of the Schmidt hammer and transmit the rebound value to the controller. The system further includes conducting an ultrasonic pulse velocity test in the vicinity of the bolt to estimate values related to the porosity, internal cracking, air voids, and water pockets of the concrete surrounding the bolt and transmit these values to the controller. The controller processing circuitry includes a memory and a database. The controller processing circuitry is configured to determine the estimated pullout load capacity for the bolt based on the rebound value of the bolt that resulted from the test event, a predetermined bolt diameter, a predetermined bolt embedment length in the concrete, and values related to the determination of the porosity, internal cracking, air voids, and water pockets around the embedded bolt. Determining the estimated pullout load capacity includes comparing, by the processing circuitry, the recorded rebound number and UPV test values with stored look up record values that associate the hammer rebound number and UPV test values to pullout load capacity so as to estimate a pullout load capacity of the bolt.

Further embodiments to an improved Schmidt hammer device are described. The improved Schmidt hammer includes at least one of a plunger with convex tip, a plunger with a guide tube and a digital level integrated into the body of the Schmidt hammer, wherein the digital level is configured to determine the inclination angle of the plunger with the vertical axis of the bolt. The processing circuitry is further configured to use the inclination angle to correct the rebound number, thus improving the accuracy of the Schmidt hammer test. Further, the user can view the angle the tip makes with the bolt vertical axis and correct the angle before taking the reading.

A further embodiment for use in determining the load carrying capacity of anchor rods, such as those used in concrete dams, nuclear power plants and tunnels, is described. The size of the Schmidt hammer and the impact energy of the plunger are increased to enable the calculation of the rebound number. The ultrasonic pulse velocity is also increased so as to enable the ultrasonic wave to traverse the region surrounding the anchor rod.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
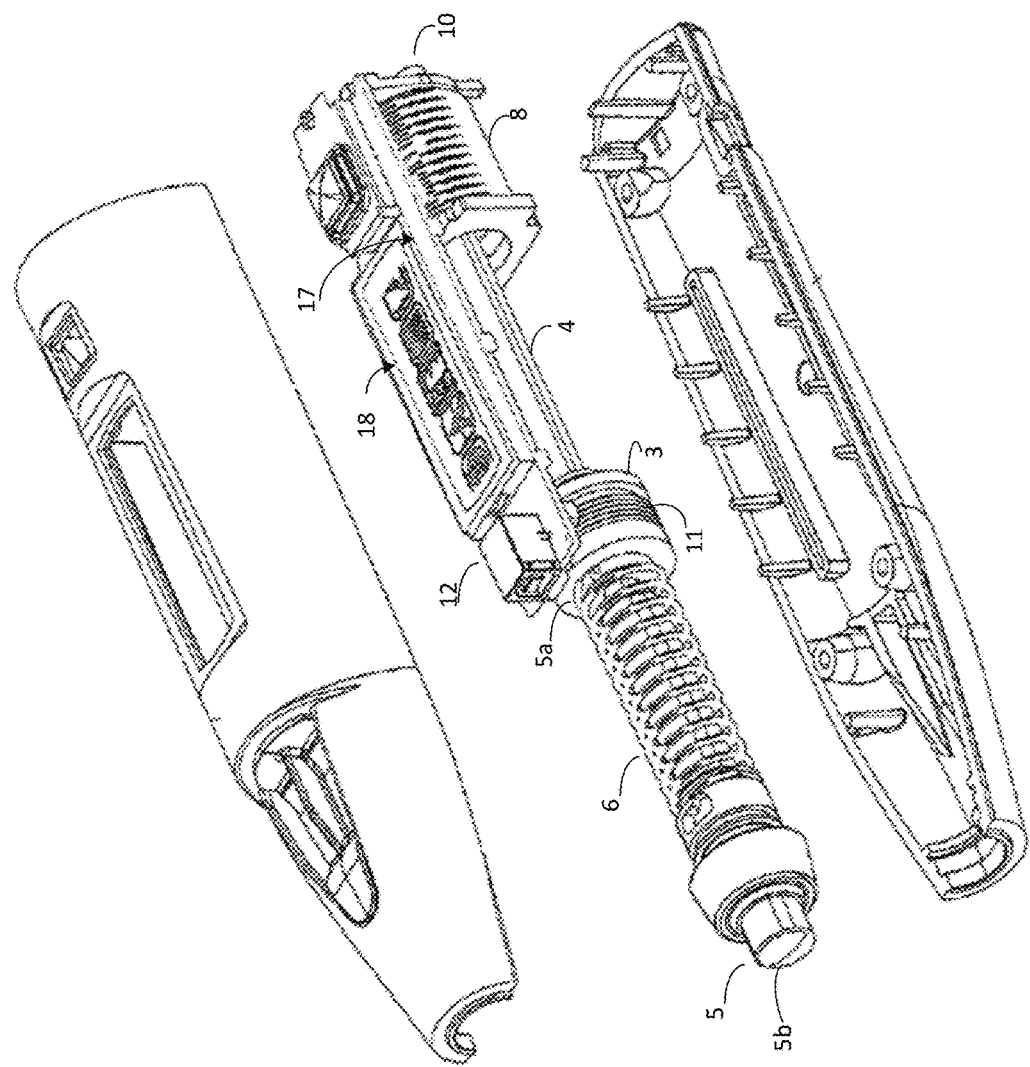
FIG. 1 is an example of a Schmidt hammer.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a device, method and system for determining the pullout load capacity of an anchor bolt embedded in concrete.

A first aspect describes the combination of ultrasonic pulse velocity tests with Schmidt hammer rebound tests to identify anchor bolts with faulty installation and to estimate their pullout load capacity by relation to the Schmidt hammer rebound value. The ultrasonic pulse velocity (UPV) test determines the bond quality of the concrete anchor bolt by relating the pulse velocity to the presence of internal cracking around the bolt. The present disclosure further improves the pullout estimate as it includes the effect of varying the embedment length on the pullout load capacity.

Combining the Schmidt hammer and the ultrasonic pulse velocity test enables users to accurately identify bolts which are improperly installed, thereby having low pullout load capacity. By taking into account the information provided by UPV test regarding the bond condition of the embedded anchor bolt, along with the rebound number, the user can effectively identity defects in the installation of anchor bolt, thus resulting in increased efficiency and accuracy in determining the pullout load capacity of the bolt and the reason for the failure of the embedment.

It is known that pullout load capacity of the bolt depends on its embedment length, diameter, bond quality/concrete strength and alignment. Ultrasonic pulse velocity tests are used to determine the quality of the bonding of the embedded anchor bolt by relating the increase in ultrasonic pulse transit time to the presence of internal pores and cracks in the vicinity of the steel bolt and the surrounding concrete. This information, combined with the Schmidt hammer rebound number, R, accurately identifies defective bolts with lower pullout load capacity.

In a further aspect, the Schmidt hammer rebound number reading is improved by the integration of a digital level into the body of the hammer. The digital level reading can be viewed on the display of the Schmidt hammer, and enables the user to correct the contact angle before taking a measurement. Further, the digital level reading can be used by the processing circuitry to correct the rebound number.

In an additional aspect, the measurement of the Schmidt hammer rebound number is improved by the addition of a guide tube around the plunger of the Schmidt hammer. The guide tube is configured to contact the concrete surface with the end of a circumferential collar, which supports and aligns the plunger with respect to the surface of the concrete, thus alleviating the possibility of slippage as the tip of the plunger contacts the anchor bolt head.

A further exemplary aspect for use in determining the load carrying capacity of anchor rods, such as those used in concrete dams, nuclear power plants and tunnels, is described. The size of the Schmidt hammer and the impact energy of the plunger are increased to enable the calculation of the rebound number. Schmidt hammers are available from manufacturers in several different energy ranges, including (i) Type L-0.735 Nm impact energy, (ii) Type N-2.207 Nm impact energy, and (iii) Type M-29.43 Nm impact energy, (See "Schmidt rebound hammers for concrete strength and rock testing", Proceq, https://www.proceq.com/compare/schmidt-hammers/).

In a further improvement, the plunger tip of the Schmidt hammer is modified to be convex, rather than concave as is commonly known. This improvement results in a more precise contact of the plunger tip with the anchor bolt head. The degree of convexity can be 5%, 10%, 15%, 20%.

Figure 2:
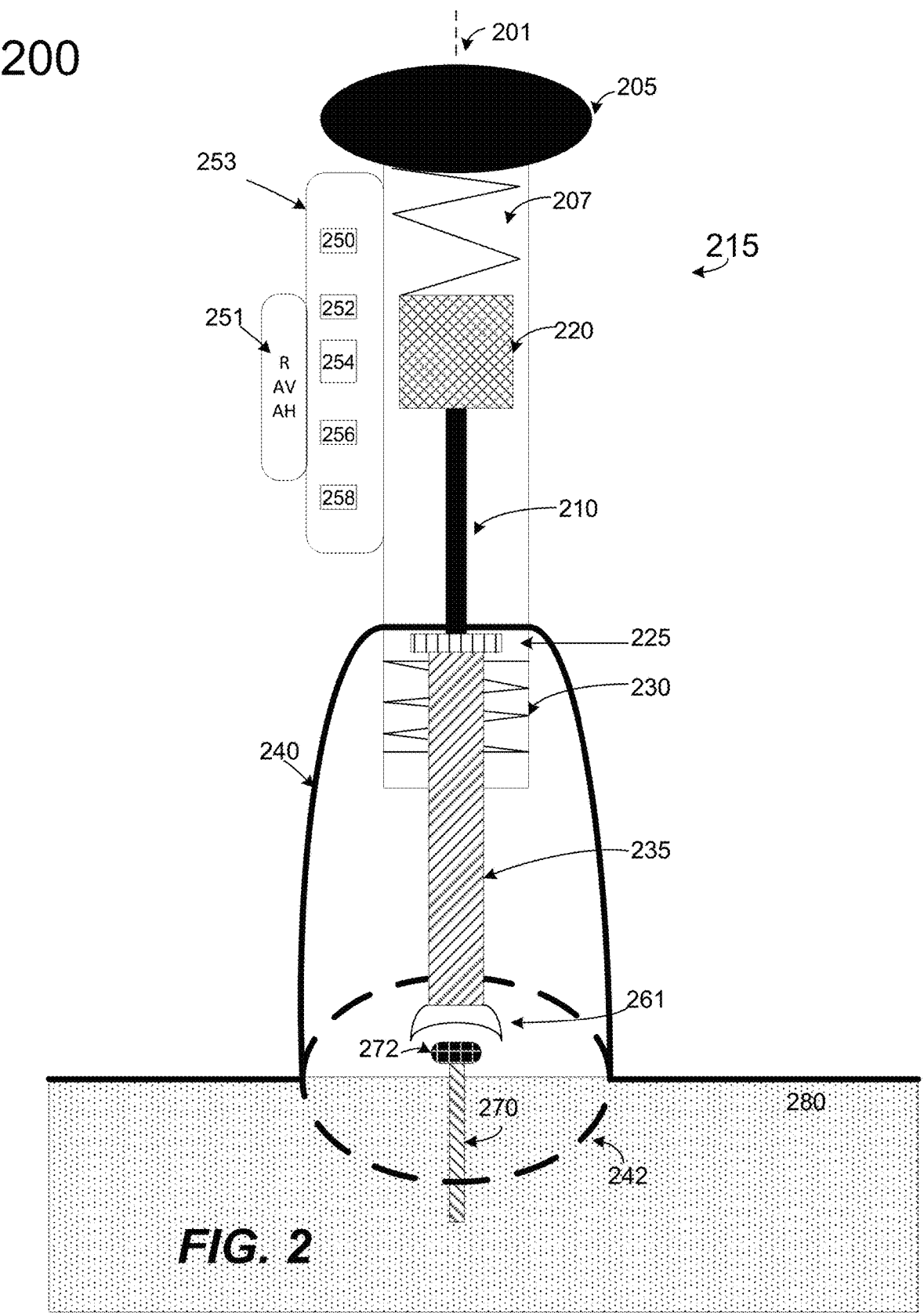
FIG. 2 is an exemplary depiction of a Schmidt hammer, according to certain embodiments.

Referring now to the drawings, wherein like reference numerals designate identical or corresponding parts throughout the several views, FIG. 2 is an example of a Schmidt hammer 215 according to certain embodiments of the disclosure. In FIG. 2, Schmidt hammer 215 may include a handle 205, a shaft 210, a plunger 235, a rebound detector 254, a data analysis module 250, a display 251, a transmitter 258, a digital level 252 and anchor bolt ID scanner 256.

In FIG. 2, the Schmidt hammer device 115 may be used to measure the rebound number, R, by impacting plunger plate 225 with impact mass 220. The mass may be driven by a trigger action spring 207 by depressing a trigger on handle 205. The plunger plate imparts the force of the impact to the plunger 210, thereby causing the convex distal tip 261 to transfer the force to the head 272 of an anchor bolt. The force travels to the end of the anchor bolt and rebounds through the head of the anchor bolt 272 to impact the distal tip 261, causing the plunger to impact the mass 220, which rebounds a distance measured by detector 254. The data analysis module 250 converts the measured distance to a rebound number.

Anchor bolt scanner 256 may scan an identification, ID, located on the head 272 of the anchor bolt and send the ID to the data analysis module to combine with the corrected rebound number in a data packet.

The digital level 252 measures the vertical and horizontal angles of inclination of the plunger with respect to concrete surface 280. The data analysis module uses the angle of inclination to correct the rebound number. The corrected rebound number, R, the vertical angle of inclination and the horizontal angle of inclination are displayed on display 251. A user is able to adjust the position of the Schmidt hammer by viewing the angles of inclination while taking the rebound number readings.

Transmitter 258 may be electrically connected to data analysis module 250 and wired to controller 305 and/or wirelessly connected to network 345 via Ethernet, WiFi, cellular, and Internet or the like. The transmitter 258 transmits the anchor bolt ID and corrected rebound number to a controller 305 connected either by wiring or wirelessly to the Schmidt hammer, as shown in FIG. 3.

Figure 3:
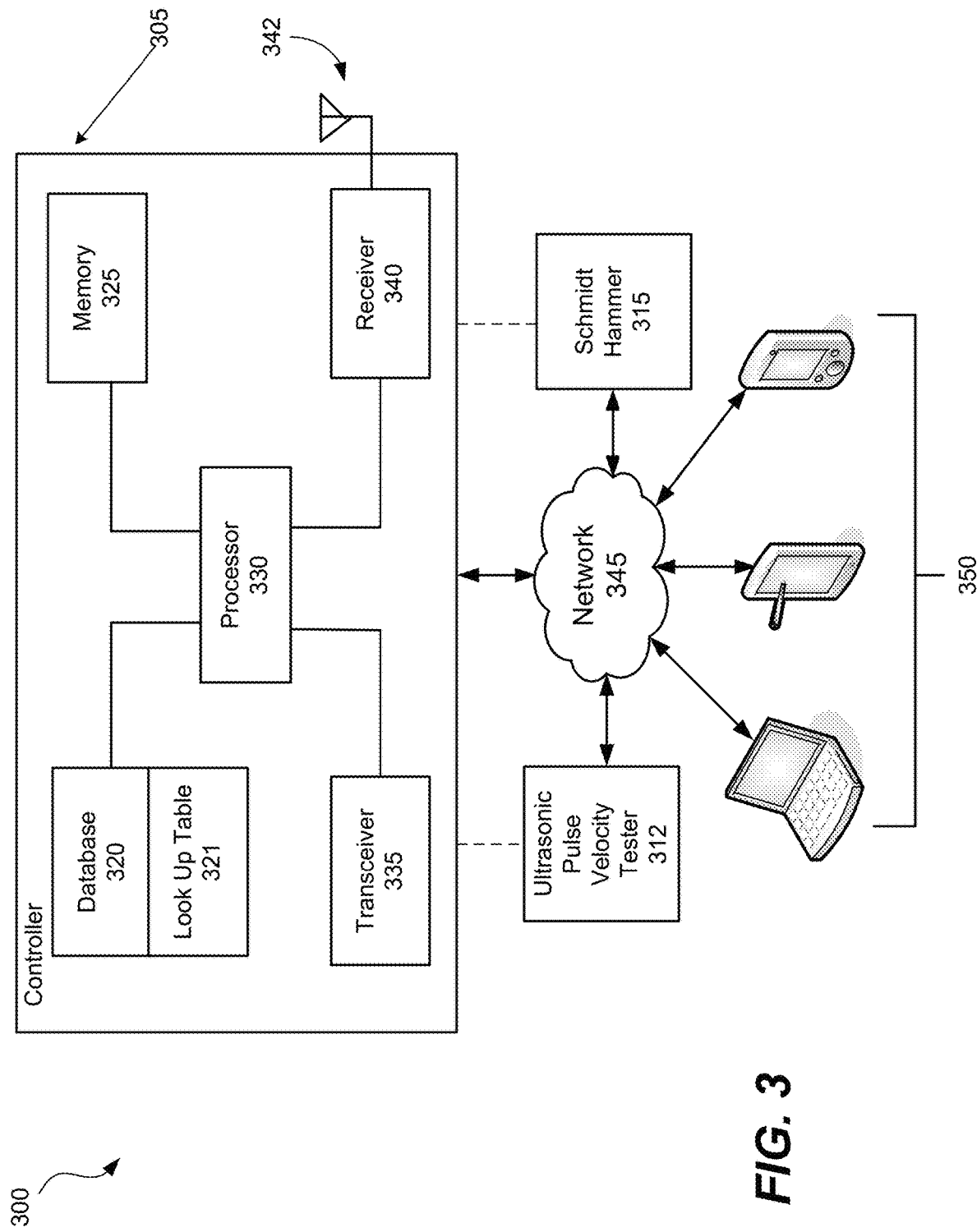
FIG. 3 is an exemplary illustration of a controller, according to certain embodiments.

FIG. 3 is a block diagram of a non-destructive device and system 300 for determining pullout capacity of anchor bolts and evaluating the bond quality of an anchor bolt embedded in concrete according to certain embodiments of the disclosure. In FIG. 3, device and system 300 may include a controller 305, a Schmidt Hammer device 315, a UPV tester 312, and a network 345.

Controller 305 may include a database 320, look up table 321, a memory 325, a processor 330, a transceiver 335, and a receiver 340. In some embodiments, database 320 may include a plurality of databases, memory 325 may include a plurality of memories, processor 330 may include a plurality of processors, transceiver 335 may include a plurality of transceivers, and receiver 340 may include a plurality of receivers. Controller 305 may be connected to network 345 via Ethernet, WiFi, cellular, and Internet or the like.

Figure 4A:
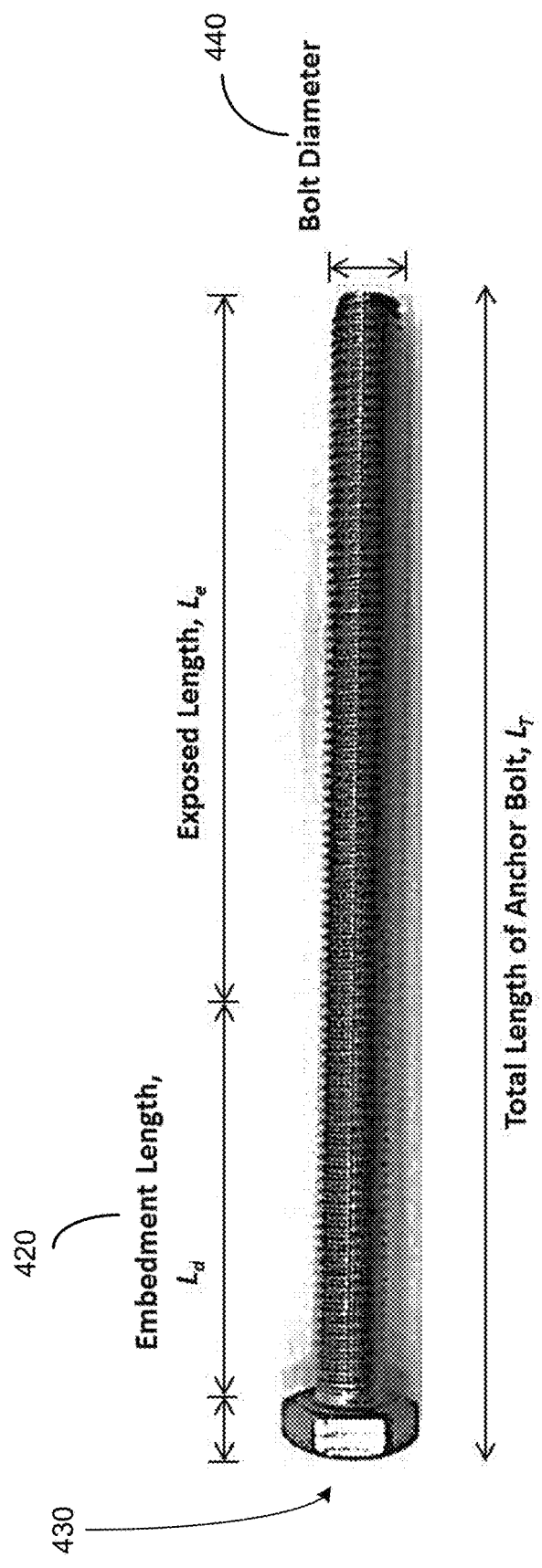
FIG. 4A is an anchor bolt, according to certain embodiments.

As illustrated by FIG. 3 and FIG. 4A, processor 330 may be configured to combine data received from Schmidt hammer device 315, such as anchor bolt identification 430, ID, and corrected rebound value, Rc, with data stored in database 320, such as anchor bolt embedment length 420, Ld, anchor bolt diameter 440, Ab, and strength of the concrete, Cs. The anchor bolt ID may be used by processor to identify the parameters Ld, Ab, and Cs. The processor 330 may match the rebound number and the embedment length, anchor bolt diameter and concrete strength to a record in look up table 321 to determine a pullout load capacity of the anchor bolt.

Network 345 may be connected via Ethernet, WiFi, cellular, Internet or the like to a remote computer 350, such as a laptop computer, a tablet computer, and/or a smartphone, or the like.

In certain embodiments, the controller 305 or remote computer 350 may be configured to monitor an installation process in real time of each anchor bolt and provide feedback to a remote installer through transceiver 315 as to whether a particular installed anchor has the required pullout load carrying capacity. The feedback may be received at installer computing device 350, which may be a computer, a laptop, a smartphone, a tablet, or any computing device capable of receiving and displaying data from network 345.

Figure 4B:
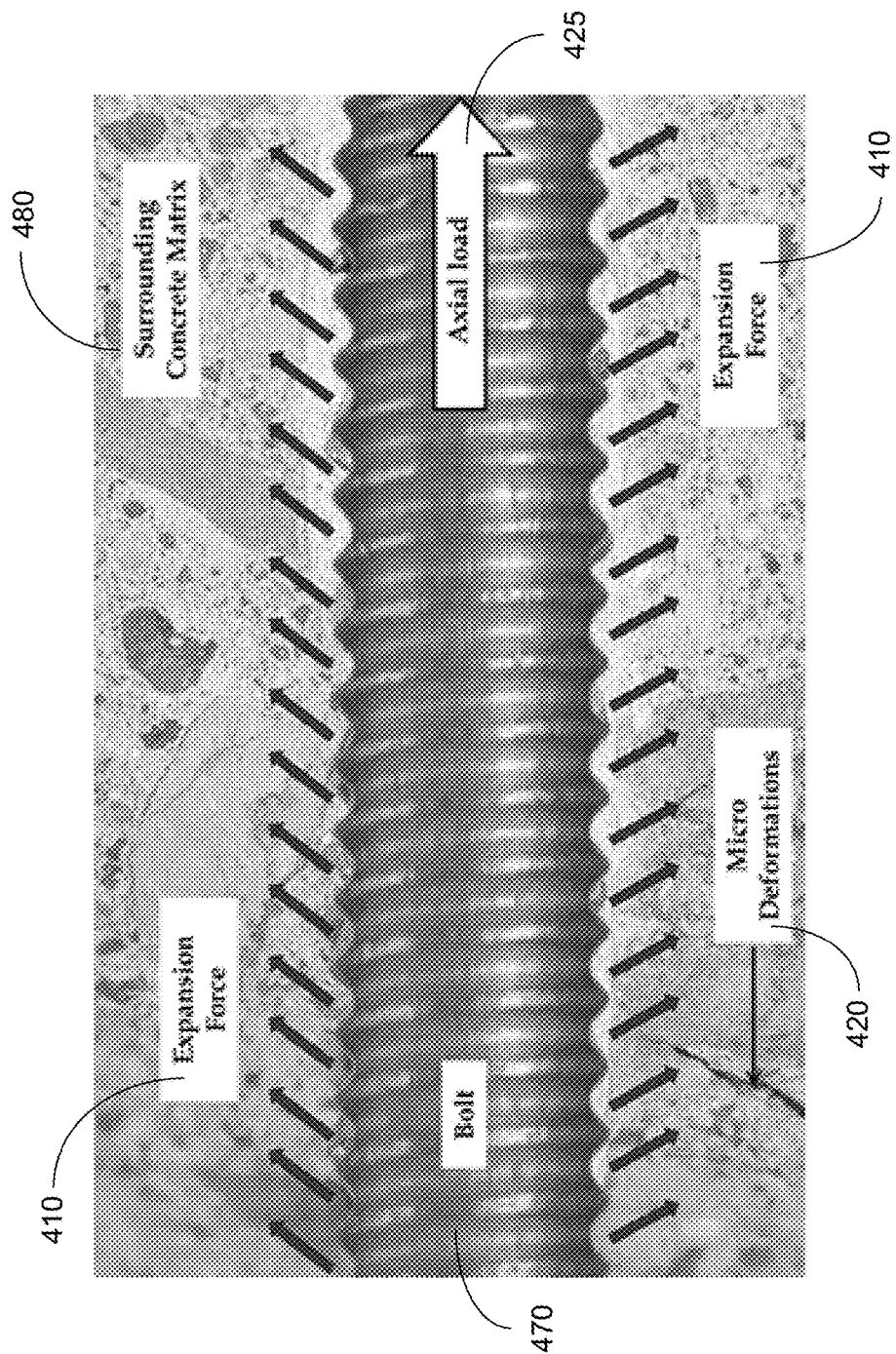
FIG. 4B is an anchor bolt embedded in concrete, according to certain embodiments.

Schmidt hammer device 315 may be configured to determine an impact load on anchor bolts. As illustrated in FIG. 4B, anchor bolts used in the construction industry are subjected to a variety of loadings during their life cycle. During the life cycle these bolts are subjected to a variety of environmental and physical loadings. Loadings vary from monotonic loading to cyclic loading to impact loading. Much research in the past has been focused on the effect of monotonic and cyclic loading. The present disclosure discusses the effect of impact loading on the load-carrying capacity of anchor bolts, for example, 8 millimeter (mm), 30 mm, and 32 mm diameter bolts with constant embedment length and concrete strength were subjected to impact loading. The impact loading is generated using a Schmidt hammer device 315, for example, a Concrete Rebound Schmidt Hammer 215 as illustrated in FIG. 2. Concrete quality, anchor alignment, anchor diameter, and water ingress are taken into consideration. An analytical model is described which takes into consideration the interfacial bonding between the bolt and surrounding concrete matrix, bolt geometric shape, diameter, alignment and embedment length. Pullout deformational response comparison between the analytical model and experimental results reveals that the model is successfully able to depict the maximum load carrying capacity and the pullout mechanism as per experimental investigation. From the analysis and presented results it is evident that the bond performance of the bolts, bolts embedded in poor quality concrete, water ingress and hidden defects can be identified by imparting the impact energy.

An aspect of the present disclosure is the combination of a pulse transit time obtained by use of an ultrasonic pulse velocity tester with the Schmidt hammer rebound readings. A non-limiting example of an ultrasonic pulse velocity tester suitable for use in the present disclosure is HC-6390 manufactured by Humboldt, 875 Tollgate Road, Elgin, Ill. 60123 https://www.humboldtmfg.com/ultrasonic-pulse-velocity-tester.html.

Figure 5A:
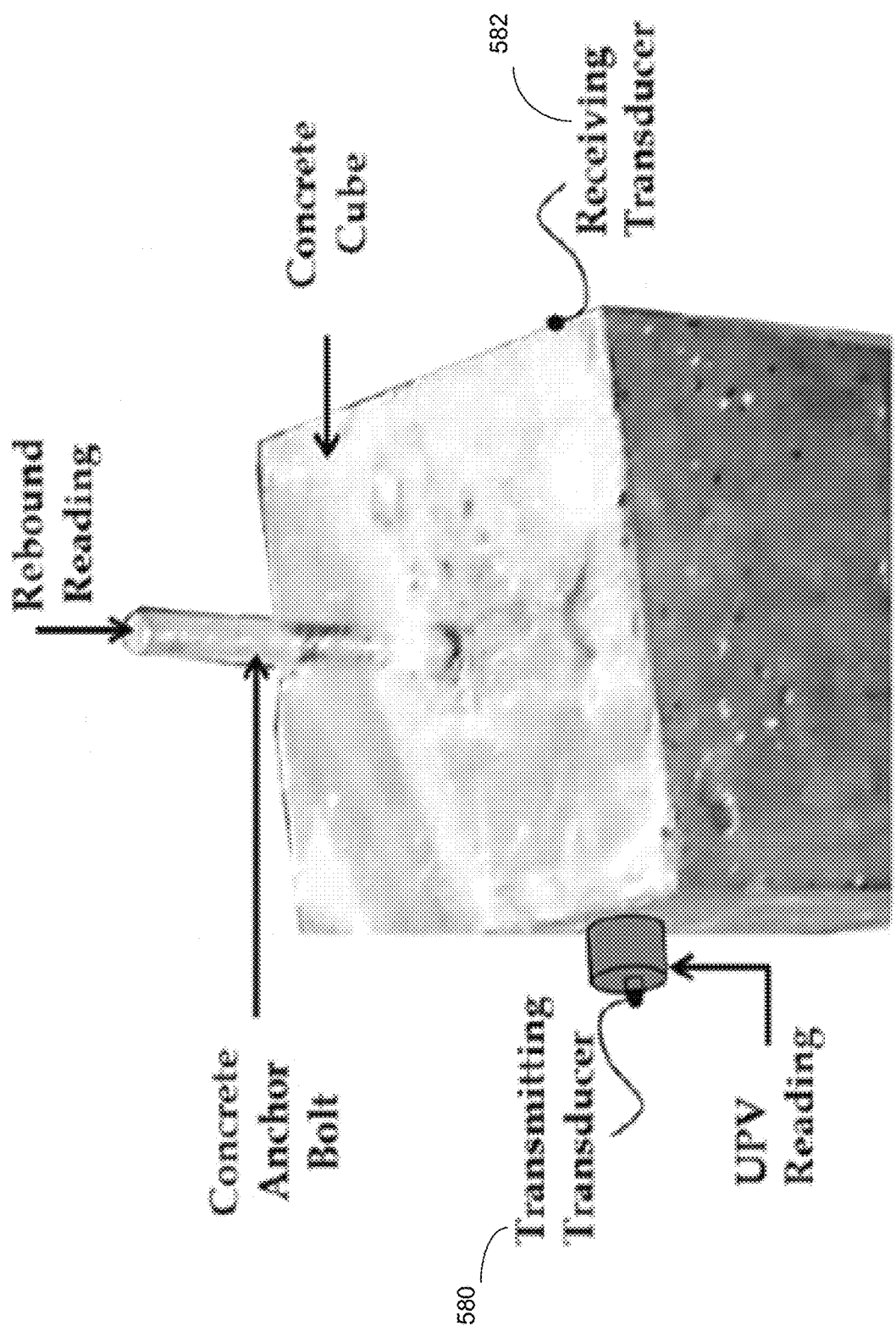
FIG. 5A is a cube specimen depicting the anchor bolt impact point and the UPV transducer placement, according to certain embodiments.
Figure 5B:
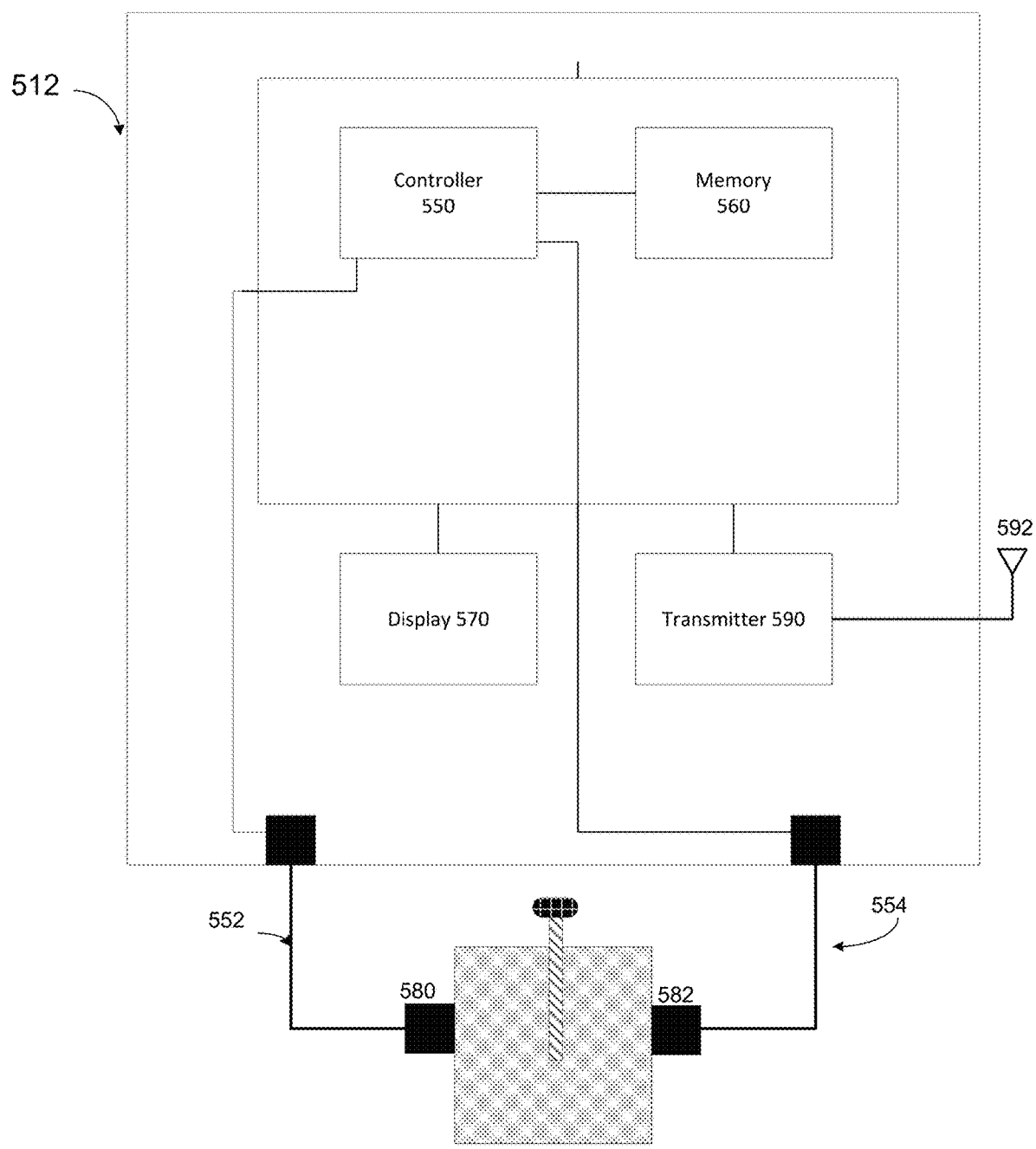
FIG. 5B is an exemplary depiction of the ultrasonic pulse velocity tester, according to certain embodiments.

An illustration of the placement of a transmitting transducer 580 and a receiving transducer 582 on a test sample is shown in FIG. 5A. As shown in FIG. 5B, the ultrasonic pulse velocity tester 500 has a controller 550 having circuitry configured to provide an electric current 552 to drive the transmitting transducer 580 to produce an ultrasonic pulse at a first time and to receive at 582 the ultrasonic pulse after it has travelled through the concrete surrounding the anchor bolt at a second time. The first time and the second time are recorded by the controller. The controller circuitry is configured to calculate the difference between the first and second times and display the difference, the transit time, TT, on ultrasonic pulse velocity tester display 570. The transit time is transmitted by transmitter 590 to the controller 305.

Processor 330 may further be configured to compare ultrasonic pulse transit times received from Ultrasonic Pulse Velocity (UPV) tester 312, to ultrasonic pulse transit time thresholds related to porosity, internal cracking, air voids, and water pockets around the embedded anchor bolt, which are stored in database 320. The processor may further be configured to generate a transit time number, TT, and values related to the porosity, internal cracking, air voids, and water pockets around the embedded anchor bolt.

The processor may combine the corrected rebound number with the transit time number, and generate a load carrying capacity number, LCC. The processor may further be configured to provide an indication of the cause of failure based on the relationship of the transit time number to the values related to the porosity, internal cracking, air voids, and water pockets around the embedded anchor bolt.

A first embodiment is described with respect to FIG. 2-5. FIG. 2 illustrates non-destructive testing device for evaluating the pullout load capacity and bond quality for anchor bolts embedded in concrete structures, and comprises a Schmidt hammer 215 including a plunger 235 having a convex distal tip 261, wherein the Schmidt hammer is configured to impart an impact force on an anchor bolt 272 in registration with the convex distal tip and to record, by means of rebound detector 254, a rebound distance travelled by the mass. The Schmidt hammer has data analysis circuitry 250 configured to determine a rebound number based on the rebound distance.

FIG. 5B illustrates an ultrasonic pulse velocity tester 500 having a transmitting transducer 552 and a receiving transducer 554, wherein the transmitting transducer is configured to contact a concrete structure at a first location surrounding the anchor bolt and the receiving transducer is configured to contact the concrete structure at a second location surrounding the anchor bolt and spaced from the first location as shown in FIG. 5A.

The ultrasonic pulse velocity tester further includes a controller 550 having circuitry configured to provide an electric current 552 to drive the transmitting transducer 580 to send an ultrasonic pulse through the concrete structure at a first time, the circuitry further configured to receive an electrical signal generated by the receiving transducer 582 based on the ultrasonic pulse at a second time, the circuitry including first processing circuitry configured to determine the transit time, TT, of the ultrasonic pulse through the concrete structure based on the difference between first time and the second time.

As shown in FIG. 3, a controller 305 is connected to the Schmidt hammer 315 and the ultrasonic pulse velocity tester 312, the controller 305 having second processing circuitry configured to correlate a Schmidt hammer rebound number with the ultrasonic pulse transit time within the concrete structure to determine a pullout load capacity and the bond quality of the embedded anchor bolt.

As shown in FIG. 2, the Schmidt hammer includes a body having a central axis 201, a proximal end (at handle 205) and a distal end (at convex tip 261) coaxially located with the central axis; an impact mass 220 coaxial with and displaceable along the central axis on guide rod 210 from the proximal end towards the distal end to impact against the plunger 235;

A drive mechanism 205, 207 for driving the impact mass along the central axis. As described above, the mass may be driven by a trigger action spring 207 by depressing a trigger (not shown) on handle 205. The plunger is coaxially located along the axis with the mass, the plunger having a proximal end, such as plunger plate 225, for receiving the impact from the impact mass.

The Schmidt hammer further includes a circuit board 253 including rebound detector 254 to measure the rebound distance; a display 251; a transmitter 258; and a data analysis module 250 to receive the rebound distance, the data analysis module 250 having circuitry configured to display the rebound number and transmit the rebound number to the controller 305.

In a further embodiment of the device, the Schmidt hammer includes a digital level 252 integrated in the body of Schmidt hammer. The digital level 252 includes a magnet and three Hall effect sensors (not shown), wherein the Hall effect sensors generate signals based on the gravitational magnetic field and the magnetic field of the magnet, and wherein the data analysis module 250 includes processing circuitry configured to receive the Hall effect signals, calculate vertical and horizontal angles of inclination of the Schmidt hammer based on the Hall effect signals, correct the rebound number based on the vertical and horizontal angles of inclination, and display the vertical and horizontal angles of inclination and the corrected rebound number on the display of the Schmidt hammer body. In this embodiment, the Schmidt hammer transmits the corrected rebound number to the controller 305.

In an additional embodiment of the device, as shown in FIG. 2, the Schmidt hammer body further comprises a guide tube 240 having a distal end 242 configured to contact the concrete surface, the guide tube configured to support alignment of the plunger with the anchor bolt in order to alleviate slippage of the distal tip on the anchor bolt.

An embodiment to a non-destructive testing method for evaluating the pullout load capacity and bond quality for anchor bolts embedded in concrete structures is described with respect to FIG. 2-5. The non-destructive testing method commences by measuring a rebound number of an anchor bolt embedded in a concrete structure by using a Schmidt hammer 315; measuring an ultrasonic pulse transit time in the concrete structure surrounding the anchor bolt by using an ultrasonic pulse velocity tester 335; estimating the pull out load carrying capacity of the installed anchor bolt by correlating the rebound number with the ultrasonic transit time; and evaluating the bond quality of the embedded anchor bolt with the concrete structure.

Measuring a rebound number includes driving a mass 220 along a central axis 201 of the Schmidt hammer to impact a plunger 235; impacting the anchor bolt head shown as 272 with a convex distal tip 261 of the plunger; measuring the rebound distance of the mass with detector 254; and generating, by the detector, a rebound number based on the rebound distance. The data analysis unit sends to rebound number to the transmitter 258, the transmitter transmitting the rebound number to a controller 305 operatively connected to the Schmidt hammer, wherein the controller is at least one of connected wirelessly to the Schmidt hammer and connected by wiring to the Schmidt hammer.

In a further embodiment of the method, a digital level 252 is used for measuring the angle of inclination of the plunger 235 integrated into the Schmidt hammer. The data analysis module uses the angle of inclination for correcting the rebound number, displaying the corrected rebound number and the angle of inclination on a display 251 of the Schmidt hammer, and transmitting the corrected rebound number to the controller.

In an additional embodiment of the method, measuring a rebound number includes contacting, with a distal end of a guide tube 240, the concrete structure 280; contacting the embedded anchor bolt 272, 270 with a convex distal tip 261 of the plunger 235; driving a mass 220 along a central axis 201 of the Schmidt hammer to impact the plunger; impacting the anchor bolt with the convex distal tip of the plunger; measuring, with detector 254, the rebound distance travelled by the mass; and generating a rebound number based on the rebound distance. As shown above, the rebound number may be corrected with respect to the angle of inclination measured by the digital level 252.

The detector may be any one of a load cell, a linear potentiometer, or an optical sensor which reads gradations or scribed areas on the mass. In a non-limiting example, the optical sensor and mass may be configured as described in U.S. Pat. No. 8,261,620, incorporated herein by reference in its entirety. A load cell may be used to measure the amount of rebound, as described in U.S publication 2017/0102304, incorporated herein by reference in its entirety.

In another embodiment of the method as shown in FIG. 3, 5A, 5B, measuring an ultrasonic pulse transit time comprises contacting the concrete structure at a first location surrounding the anchor bolt with a transmitting transducer 580; contacting the concrete structure at a second location surrounding the anchor bolt and spaced from the first location with a receiving transducer 582; generating due to an electric current 552 transmitted by controller 550, an ultrasonic pulse with the transmitting transducer at a first time; receiving the ultrasonic pulse with the receiving transducer at a second time later than the first time, the receiving transducer generating an electrical signal 554 in response to receiving the ultrasonic pulse; calculating, by controller 550 which includes processing circuitry configured for calculating, the ultrasonic pulse transit time, TT, by subtracting the first time from the second time; recording the ultrasonic pulse transit time in a memory 560 of the ultrasonic pulse velocity tester, displaying the ultrasonic pulse transit time on a display 570 of the ultrasonic pulse velocity tester 512, transmitting, by transmitter 590 and antenna 592, the ultrasonic pulse transit time to a controller 305 connected to the ultrasonic pulse velocity tester 512, wherein the controller is at least one of connected wirelessly to the ultrasonic pulse velocity tester and connected by wiring to the ultrasonic pulse velocity tester.

The method continues by estimating the pull out load capacity of the embedded anchor bolt by receiving the Schmidt hammer rebound number, R, at the controller, wherein FIG. 3 illustrates the controller including a database 320, the database including a look up table 321 of values related to pull out load capacity, a memory 325, a processor 330, a transceiver 335 and a receiver 340; retrieving, from data stored in the database, an embedment length, Ld, an anchor bolt diameter and a concrete strength as shown in FIG. 4.

The method includes by the processor combining the Schmidt hammer rebound number, R, with the embedment length, Ld, anchor bolt diameter, Bd, and concrete strength, Cs, to generate a vector x, where x={R, Ld, Bd, Cs}; receiving the transit time, TT, from the ultrasonic pulse velocity tester at the controller; combining the transit time with the with the vector x to generate a vector y, where y={R, Le, Bd, Cs, TT} and matching the vector y with a record from the look up table 321 stored in the database 320, wherein the lookup table record relates the vector y to a pull out load capacity.

The method proceeds by evaluating the bond quality of the embedded anchor bolt with the concrete structure, by receiving the Schmidt hammer rebound number at the controller, wherein the controller includes a database, a memory, a processor, a transceiver and a receiver; retrieving, from data stored in the database, an embedment length, anchor bolt diameter and concrete strength; combining the Schmidt hammer rebound number, R, with the embedment length, Ld, anchor bolt diameter, Bd, and concrete strength, Cs, to generate a vector x, where x={R, Le, Bd, Cs}; receiving the transit time, TT, from the ultrasonic pulse velocity tester at the controller, comparing the transit time, TT, to ultrasonic pulse transit time thresholds stored in the database, the ultrasonic pulse transit time thresholds related to porosity, P, internal cracking, IC, air voids, AV, and water pockets, W, around the embedded anchor bolt; generating a vector z, where $z_i$={TT, $P_i$, $IC_i$, $AV_i$, $W_i$} and $P_i$=1 if TT≥P and $P_i$=0 if TT≤P, $IC_i$=1 if TT≥IC and $IC_i$=0 if TT≤IC, $AV_i$=1 if TT≥AV and $AV_i$=0 if TT≤AV, and $P_i$=1 if TT≥P and $P_i$=0 if TT≤P; where i is an integer, adding the vector z to the vector x to generate a vector k, where $k_i$={R, Le, Bd, Cs, TT, $P_i$, $IC_i$, $AV_i$, $W_i$}; matching the vector $k_i$ with a record from a look up table stored in the database, wherein the lookup table record relates the values of the vector $k_i$ to the bond quality of the embedded anchor bolt with the concrete structure.

In a further embodiment of the method, measuring the rebound number includes measuring the angle of inclination of the plunger with a digital level 252 integrated into the Schmidt hammer 215; correcting the rebound number based on the angle of inclination; displaying the corrected rebound number and the angle of inclination on a display 251 of the Schmidt hammer; transmitting the corrected rebound number, Rc, to the controller; generating a vector kc, where $kc_i$={R, Le, Bd, Cs, TT, $P_i$, $IC_i$, $AV_i$, $W_i$}, where i is an integer greater than 0 and less than N, where N is the number of readings taken; matching the vector kc with a record from a look up table stored in the database, wherein the lookup table record relates the values of the vector kc to the bond quality of the embedded anchor bolt with the concrete structure.

An embodiment of a non-destructive testing system evaluating the pullout load capacity and bond quality for anchor bolts embedded in concrete structures follows as illustrated by FIG. 2-5.

The system includes measuring, by a Schmidt hammer 315, a rebound number of an anchor bolt embedded in a concrete structure; measuring, by an ultrasonic pulse velocity tester 312, an ultrasonic pulse transit time in the concrete structure 280 surrounding the anchor bolt (272, 270); estimating, by a controller 305 including processing instructions configured to analyze the rebound number and the ultrasonic transit time, the pull out load carrying capacity of the installed anchor bolt; and evaluating, by the controller, the bond quality of the embedded anchor bolt with the concrete structure. Measuring a rebound number further comprises driving, by means of a spring loaded trigger device (205, 207), a mass 220 along a central axis 201 of the Schmidt hammer to impact a plunger 210, the plunger having a convex distal tip 261; impacting the anchor bolt head 272 with the convex distal tip of the plunger; measuring, by means of a rebound detector 254, the rebound distance of the mass; generating, by means of a data analysis module 250 of the Schmidt hammer, a rebound number based on the rebound distance; measuring, by a digital level 252 integrated into the Schmidt hammer, the angle of inclination of the plunger; correcting, by the data analysis module, the rebound number based on the angle of inclination; displaying, on a display 251 of the Schmidt hammer, the corrected rebound number and the angle of inclination; and transmitting, by a transmitter 258 of the Schmidt hammer, the corrected rebound number, Rc, to a controller 305 operatively connected to the Schmidt hammer, wherein the controller is at least one of connected wirelessly to the Schmidt hammer and connected by wiring to the Schmidt hammer.

In the system, measuring an ultrasonic pulse transit time comprises contacting the concrete structure at a first location surrounding the anchor bolt with a transmitting transducer 580; contacting the concrete structure at a second location surrounding the anchor bolt and spaced from the first location with a receiving transducer 582; generating, with the transmitting transducer, an ultrasonic pulse at a first time; receiving, with the receiving transducer, the ultrasonic pulse at a second time later than the first time, the receiving transducer generating an electrical signal 554 in response to receiving the ultrasonic pulse; calculating, by a controller of the ultrasonic pulse velocity tester having processing circuitry configured to calculate, the ultrasonic pulse transit time by subtracting the first time from the second time; recording, in a memory 560 of the ultrasonic pulse velocity tester, the ultrasonic pulse transit time; and displaying, on a display 570 of the ultrasonic pulse velocity tester, the ultrasonic pulse transit time; transmitting, by a transmitter 590 of the ultrasonic pulse velocity tester, the ultrasonic pulse transit time to a controller 305 connected to the ultrasonic pulse velocity tester 512, wherein the controller is at least one of connected wirelessly to the ultrasonic pulse velocity tester and connected by wiring to the ultrasonic pulse velocity tester.

In the described system, estimating the pull out load capacity of the embedded anchor bolt further comprises receiving, by the receiver 340 of the controller, the corrected Schmidt hammer rebound number, Rc, wherein the controller includes a database, a memory, a processor, a transceiver and a receiver; retrieving, from data stored in the database, an embedment length, an anchor bolt diameter and a concrete strength; combining, by the processor, the Schmidt hammer rebound number, Rc, with the embedment length, Ld, anchor bolt diameter, Bd, and concrete strength, Cs, to generate a vector x, where x={R, Ld, Bd, Cs}; receiving, by the receiver of the controller, the transit time, TT, from the ultrasonic pulse velocity tester; combining, by the processor, the transit time with the with the vector x to generate a vector y, where y={R, Le, Bd, Cs, TT}; matching, by the processor, the vector y with a record from a look up table stored in the database, wherein the lookup table record relates the vector y to a pull out load capacity.

In the system, evaluating the bond quality of the embedded anchor bolt with the concrete structure comprises receiving, by the receiver of the controller, the corrected Schmidt hammer rebound number, wherein the controller includes a database, a memory, a processor, a transceiver and a receiver; retrieving, from data stored in the database, an embedment length, an anchor bolt diameter and a concrete strength; combining, by the processor, the corrected Schmidt hammer rebound number, Rc, with the embedment length, Ld, anchor bolt diameter, Bd, and concrete strength, Cs, to generate a vector x, where x={Rc, Le, Bd, Cs}; receiving, by the receiver of the controller, the transit time, TT, from the ultrasonic pulse velocity tester 312; comparing, by the processor, 330 the transit time, TT, to ultrasonic pulse transit time thresholds stored in the database, the ultrasonic pulse transit time thresholds related to porosity, P, internal cracking, IC, air voids, AV, and water pockets, W, around the embedded anchor bolt; generating, by the processor, a vector z, where $z_i=\{TT, P_i, IC_i, AV_i, W_i\}$ and $P_i=1$ if $TT \geq P$ and $P_i=0$ if $TT \leq P$, $IC_i=1$ if $TT \geq IC$ and $IC_i=0$ if $TT \leq IC$, $AV_i=1$ if $TT \geq AV$ and $AV_i=0$ if $TT \leq AV$, and $P_i=1$ if $TT \geq P$ and $P_i=0$ if $TT \leq P$; where i is an integer greater than 0 and less than N, where N is the number of readings taken; adding, by the processor, the vector z to the vector x to generate a vector k, where $k_i=\{R, Le, Bd, Cs, TT, P_i, IC_i, AV_i, W_i\}$; and matching, by the processor, the vector k with a record from a look up table stored in the database, wherein the lookup table record relates the values of the vector $k_1$ to the bond quality of the embedded anchor bolt with the concrete structure.

Experimental Testing:

An experimental test was conducted to verify the efficacy of combining Schmidt hammer rebound testing with ultrasonic pulse velocity testing.

In a non-limiting example as shown in FIG. 4A, 4B, 12 mm diameter bolts with embedment length of 70 mm and 50 mm were tested using normal strength concrete. Pullout load capacity versus the Schmidt hammer rebound number for each embedment length is determined.

Figure 6:
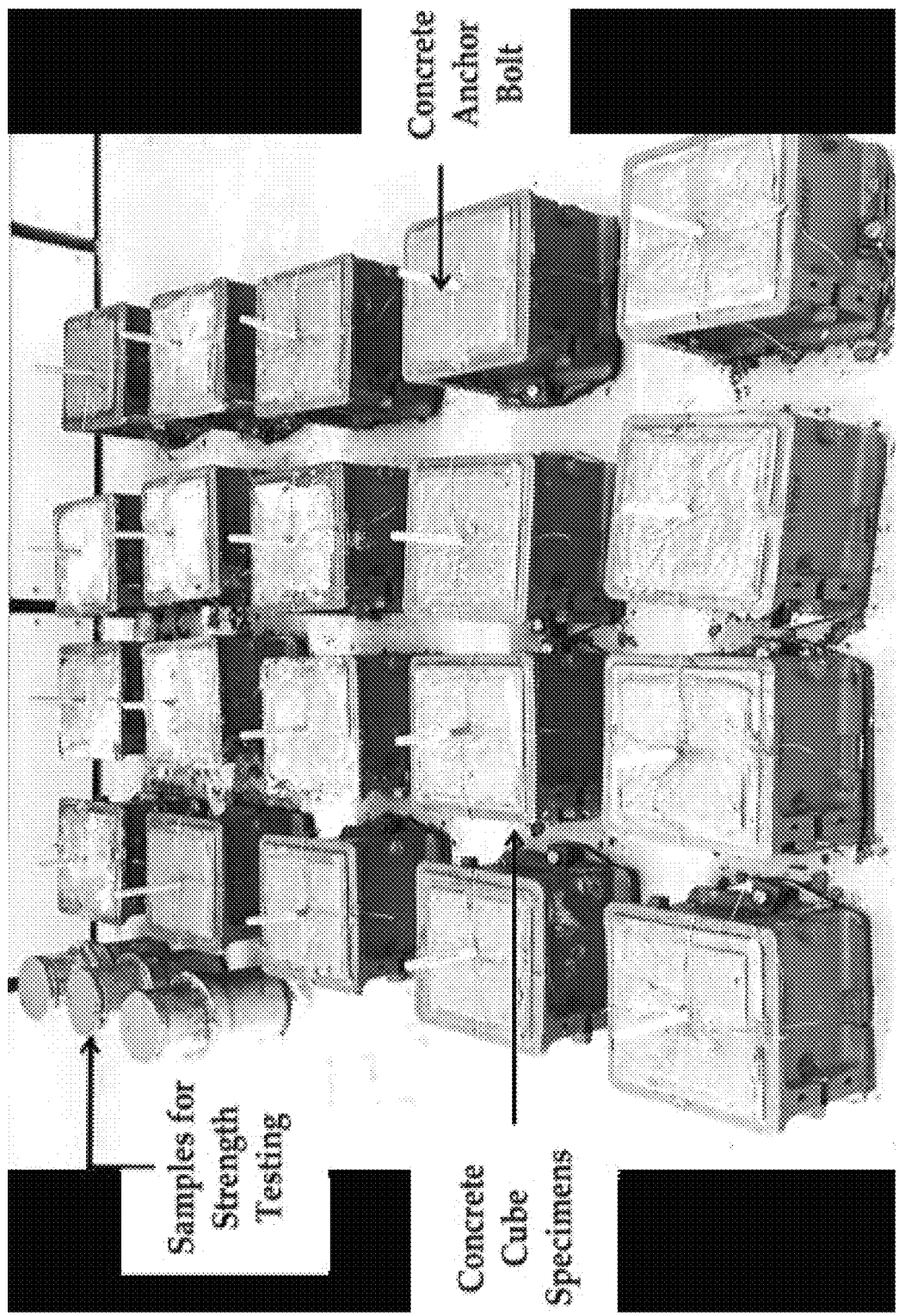
FIG. 6 is an exemplary illustration of concrete samples prepared for testing embedded anchor bolts, according to certain embodiments.
Figure 7:
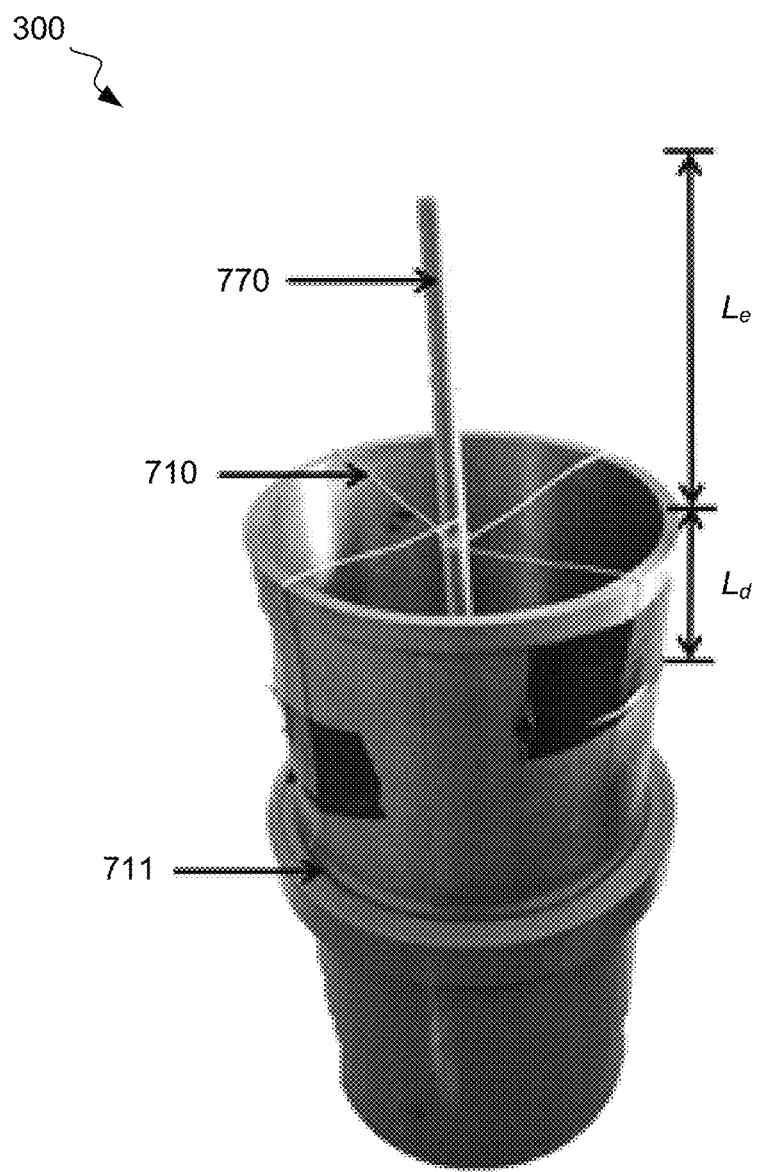
FIG. 7 is an illustration of guidewires for holding the anchor bolts during concrete pouring, according to certain embodiments.

Forty 150×150×150 mm cube specimens and six 150×300 cylindrical specimens for compressive strength testing were cast as shown in FIG. 6, using ordinary Portland cement (Type I) with a specific gravity of 3.15 in accordance with ASTM C150. The chemical composition of OPC by weight (%) was as follows: $CaO=64.3$, $SiO_2=22$, $Al_2O_3=5.64$, $Fe_2O_3=3.8$, $MgO=2.11$, Others=2.15. Desert sand was used as fine aggregate possessing bulk specific gravity and water absorption of respectively, 2.66 and 0.60%. The water cement ratio of 0.41 with water content was 120; cement 290 kg/m3, air entrainment 4.2%; sand and gravel 828 and 1043 kg/m3, respectively. Limestone course aggregate with a maximum size of 19 mm was used and graded in accordance with ASTM C33, having a bulk specific gravity and water absorption of 2.45 and 2.05%, respectively. The slump was 100+25 mm. Curing was done in the temperature controlled water tank and the average 28 days compressive strength was 34.1 MPa. Preconstruction installed steel anchor bolts with varying embedment length were investigated as shown in FIG. 4C. The total length, LT, of the anchor bolt was 150 mm, the embedment lengths, Ld, were 50 mm and 70 mm and the exposed lengths, Le, were 100 mm and 80 mm respectively. The anchor bolt was centered in the middle of the cube mold with the help of guide wires 710 as shown in FIG. 7. The embedment depth was also maintained using the guide wire mechanism. FIG. 6 shows the prepared sample after curing. Five rebound readings of Schmidt hammer were recorded on protruding end of the anchor bolt and the average value of these readings were used for analysis.

During the reading and recording procedure, care was taken to vertically align the bottom of anchor bolt to the tip of Schmidt hammer, and this verticality was ensured through visual inspection. The vertical alignment of the anchor bolt with the concrete surface plays a crucial role in its load carrying capacity. Anchor bolts with skewed alignment greater than 15 degrees are not suitable for rebound testing as the tip of the rebound hammer will slip off the bolt surface. The alignment was measured using an image analysis technique in which the image of a poorly aligned anchor bolt was superimposed on that of an aligned anchor bolt and the alignment angle was recorded in degrees.

Figure 8:
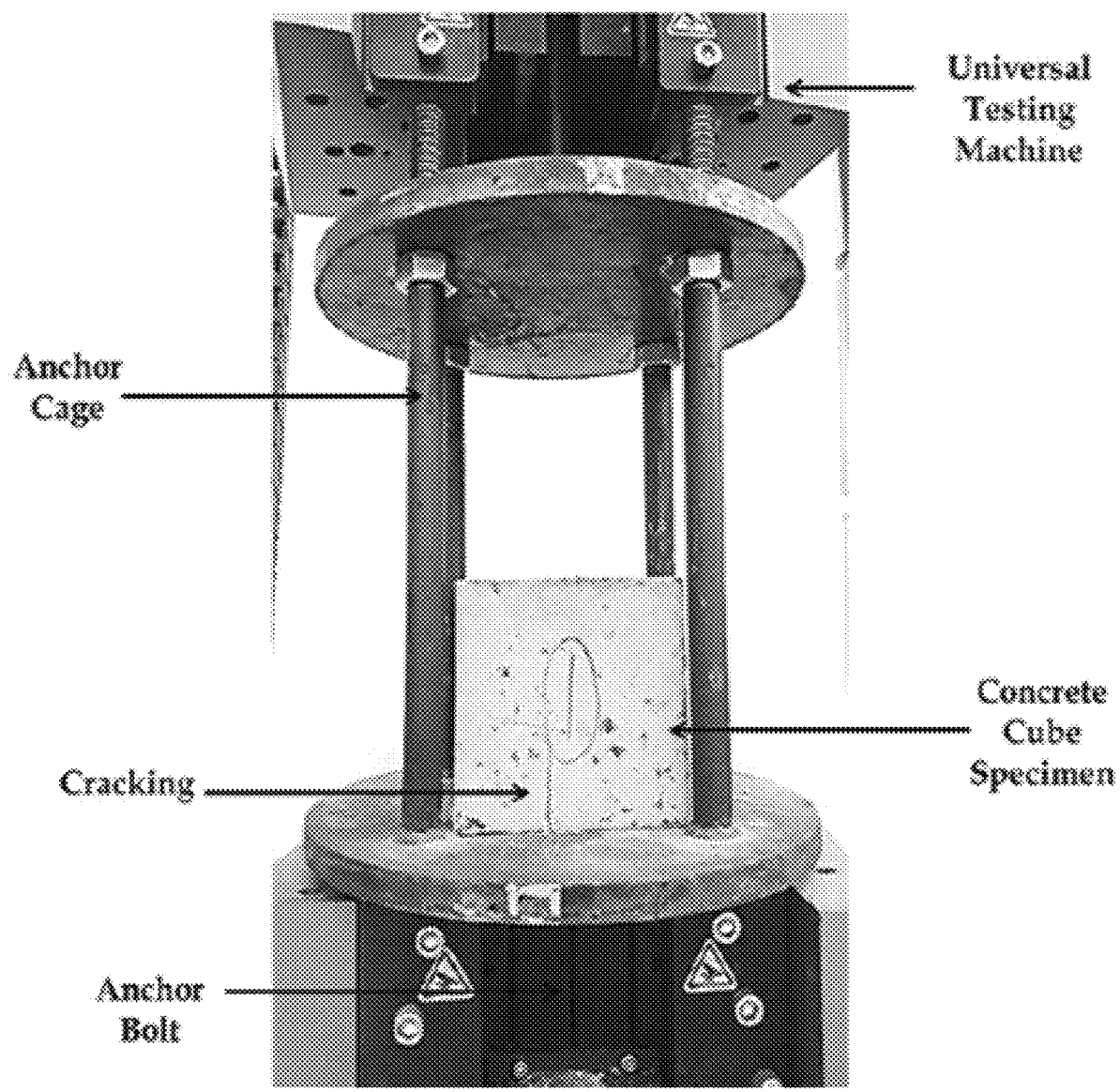
FIG. 8 is an illustration of a pullout testing setup, according to certain embodiments.
Figure 9:
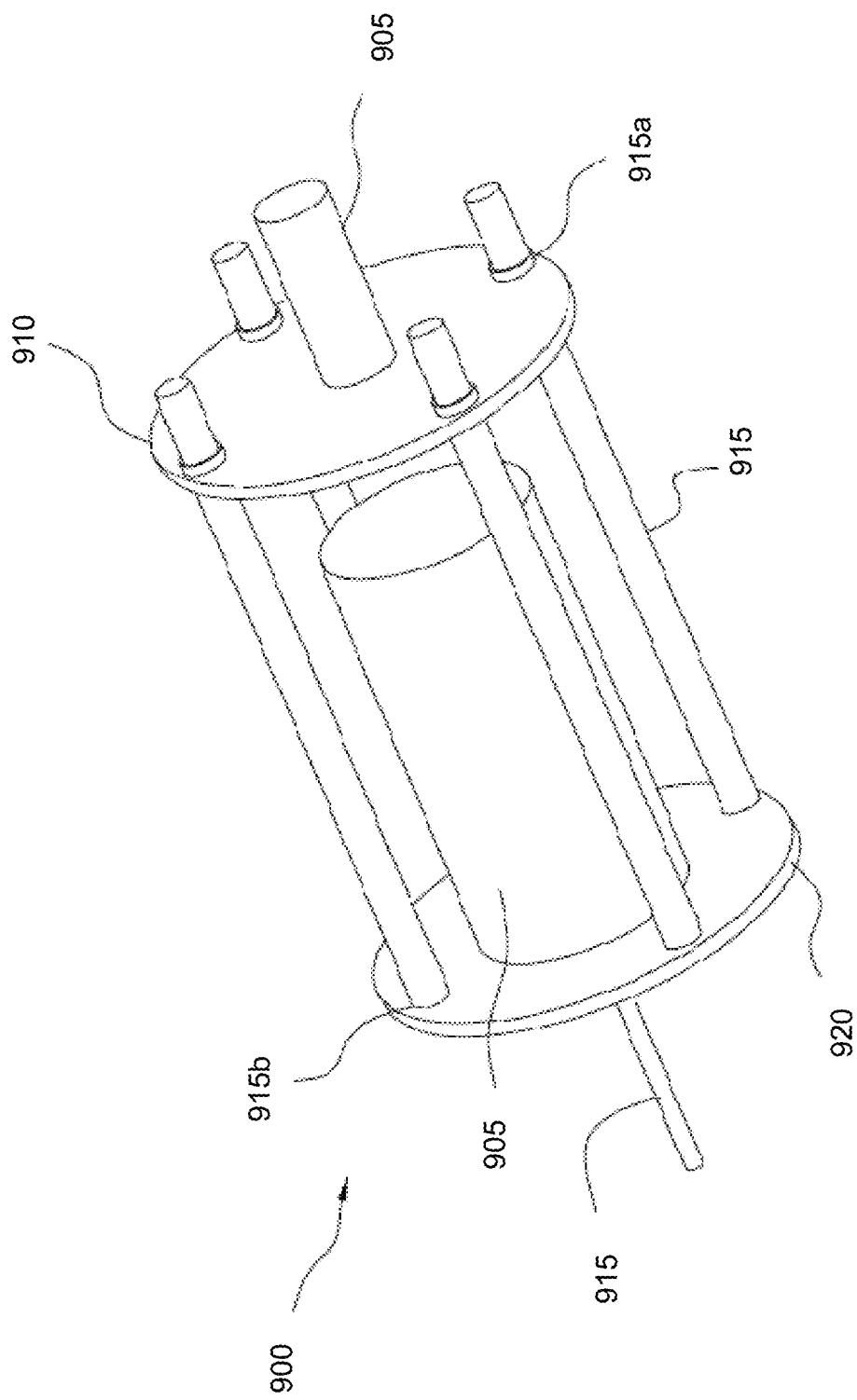
FIG. 9 is an exemplary schematic diagram of an anchor cage used in testing, according to certain embodiments.

FIG. 8 presents the pull out test setup. An anchor cage as shown in FIG. 9 can be employed to conduct pull out strength testing with the help of universal testing machine (UTM). The cube specimens were inserted in the anchor cage and whole assembly was fixed in the UTM. This test setup is not only economical as it overcomes the need of a separate pull out testing device but it also has the added benefit that the pull out load versus displacement plots can be obtained from the UTM directly, eliminating the need for complex data recording set-up, LVDTs and measuring gauges.

Figure 10:
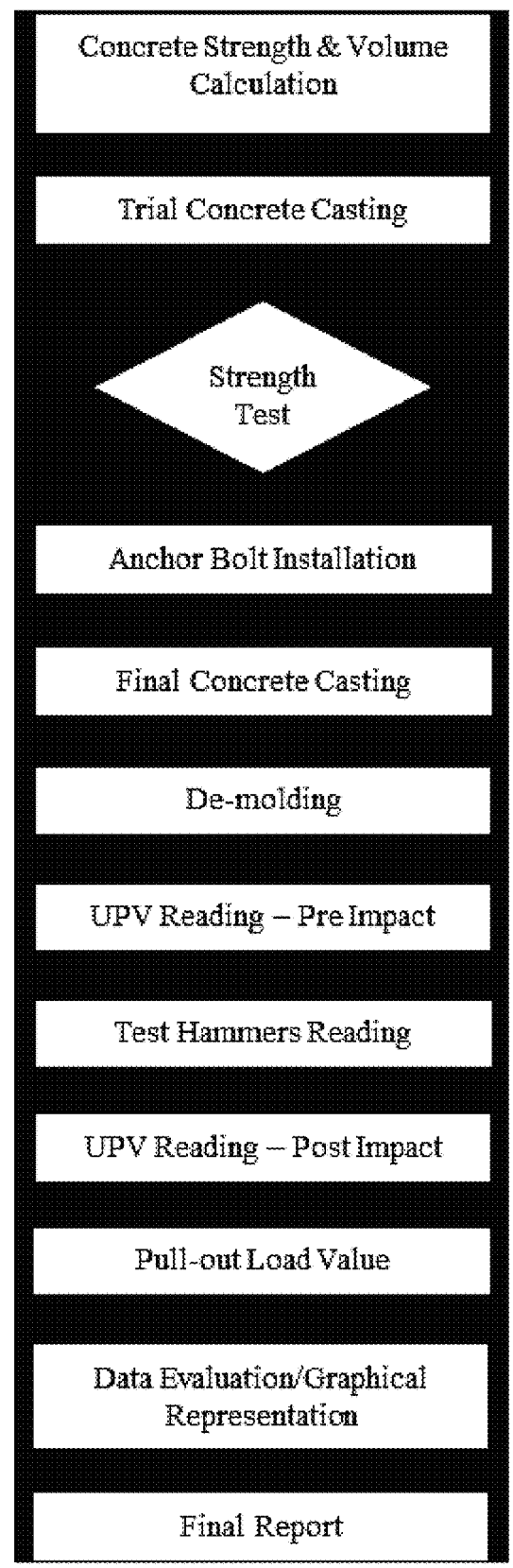
FIG. 10 is a flow chart of the testing steps, according to certain embodiments.

FIG. 10 presents a flow chart of the test method steps for determining the rebound number and the UPV reading. A trial concrete mix was prepared and assessed for strength. Anchor bolts were installed in empty concrete cubes prior to concrete casting. The embedment depth and the bolt alignment were adjusted using guide wires. Concrete mix was poured and, after curing, the samples were demolded and guide wires were removed in order to avoid any interference with the ultrasonic pulse velocity testing. UPV readings were recorded in accordance with ASTM C597 (See ASTM Test Designation C 597-02, "Standard Test Method for Pulse Velocity through Concrete", Annual Book of ASTM Standards, West Conshohocken, Pa., Vol. 4, No. 2. 2003).

The sample dimension, aggregate size, size of anchor bolt, frequency, concrete moisture condition, temperature and the presence of anchor bolt perpendicular to the pulse propagation path were all taken into consideration in accordance with BS 1881, RILEM and Tarun et al. (See BS 1881, Part 203. "Recommendations for Measurement of Velocity of Ultrasonic Pulses in Concrete", British Standards Institution, London, 1986; RILEM Recommendation NDT 1. "Testing of concrete by the ultrasonic pulse method", RILEM Publications, Paris, 1972; Tarun, R. N., Malhotra, M. V. and Popovics, S. J. "The Ultrasonic Pulse Velocity Method", CRC Press LLC, London, each incorporated herein by reference in its entirety). Furthermore, the transducer 580 and receiver 582 were firmly placed on the opposite ends of the cube as shown in FIG. 5A; and petroleum jelly was used to ensure proper coupling between the transducer and a the cube specimen. The wave velocity was calculated by dividing the fastest time in microsecond (µs), taken by the ultrasonic wave to travel through the 150 mm width of the specimen. A 54 kHz frequency with a wavelength of 68 mm in was chosen for the normal strength concrete with the maximum aggregate size of 19 mm.

Prior to testing, the UPV testing equipment is calibrated and it is verified that no air pockets exist between the transducer and the concrete cube. Three reading locations were chosen along the embedment depth of anchor bolt. Furthermore, three readings were recorded at each location. The shortest transit time corresponding to the fastest wave travel time was recorded, as wave velocity is affected by proper coupling, thus the fastest travel time represents an optimum coupling.

Factors affecting the bond performance of the embedded anchor bolt were taken into consideration and a consistent quality of concrete was used to ensure uniformity in the bond quality along the embedment length of anchor bolt. A correction factor of 0.98 related to the presence of 12 mm Φ diameter anchor bolt present perpendicular to the propagation path of ultrasonic pulse was applied to all the reported readings in the test. Furthermore, all the UPV testing was conducted on air dried samples after 28 days of curing and amplitude and shape of the received sinusoidal waveforms were recorded.

Figure 11:
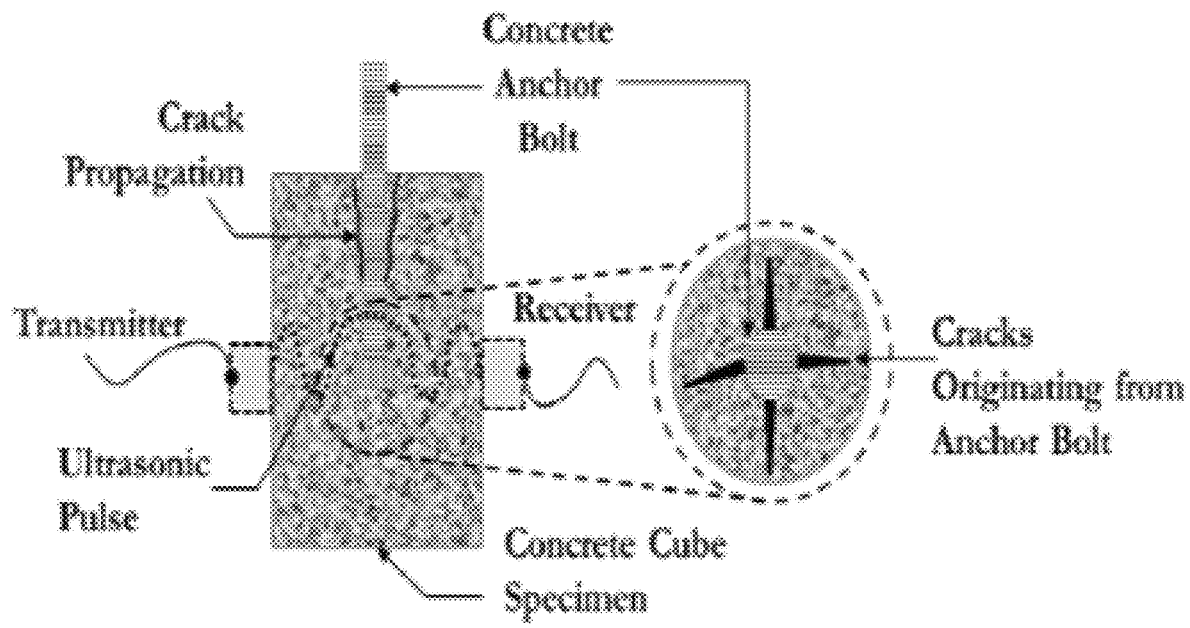
FIG. 11 is a conceptual diagram of crack propagation around the embedded anchor bolt, according to certain embodiments.

Casting of the concrete samples was conducted in three layers of equal thickness and a tamping rod was used to compact the concrete. Twenty five evenly distributed blows were imparted to each layer and the concrete surface was leveled using a trowel. Since the bond quality of the anchor bolt seating plays a crucial role on its overall load carrying capacity, much care was taken to compact the concrete layers. It was noticed during testing that concrete samples with poor quality concrete displayed a longer transit time for the ultrasonic pulse to travel through the concrete cube. A set of five readings were recorded on the top of each anchor bolt as shown in FIG. 5A. The energy imparted by the Schmidt hammer is transferred to the concrete surrounding the anchor bolt. Strongly bonded bolts were successfully able to transfer the impact energy to the surrounding concrete, resulting in a higher rebound number. Bolts having a bond with porous concrete were unable to transfer the impact energy. This poor bond was exhibited by cracking in the concrete surrounding the steel anchor bolt, and led to a lower rebound number. Further, the presence of internal cracking was successfully detected through the use of ultrasonic pulse velocity test. FIG. 11 shows internal cracking at the concrete steel interface. The velocity of the ultrasonic wave is faster in the perfect bond specimens while the specimens with lower bond quality resulted in slower transit time for the same path length. The combination of rebound number with UPV test identified anchor bolts with poor concrete bonds, thereby resulting in lower pullout load capacity.

Figure 12A:
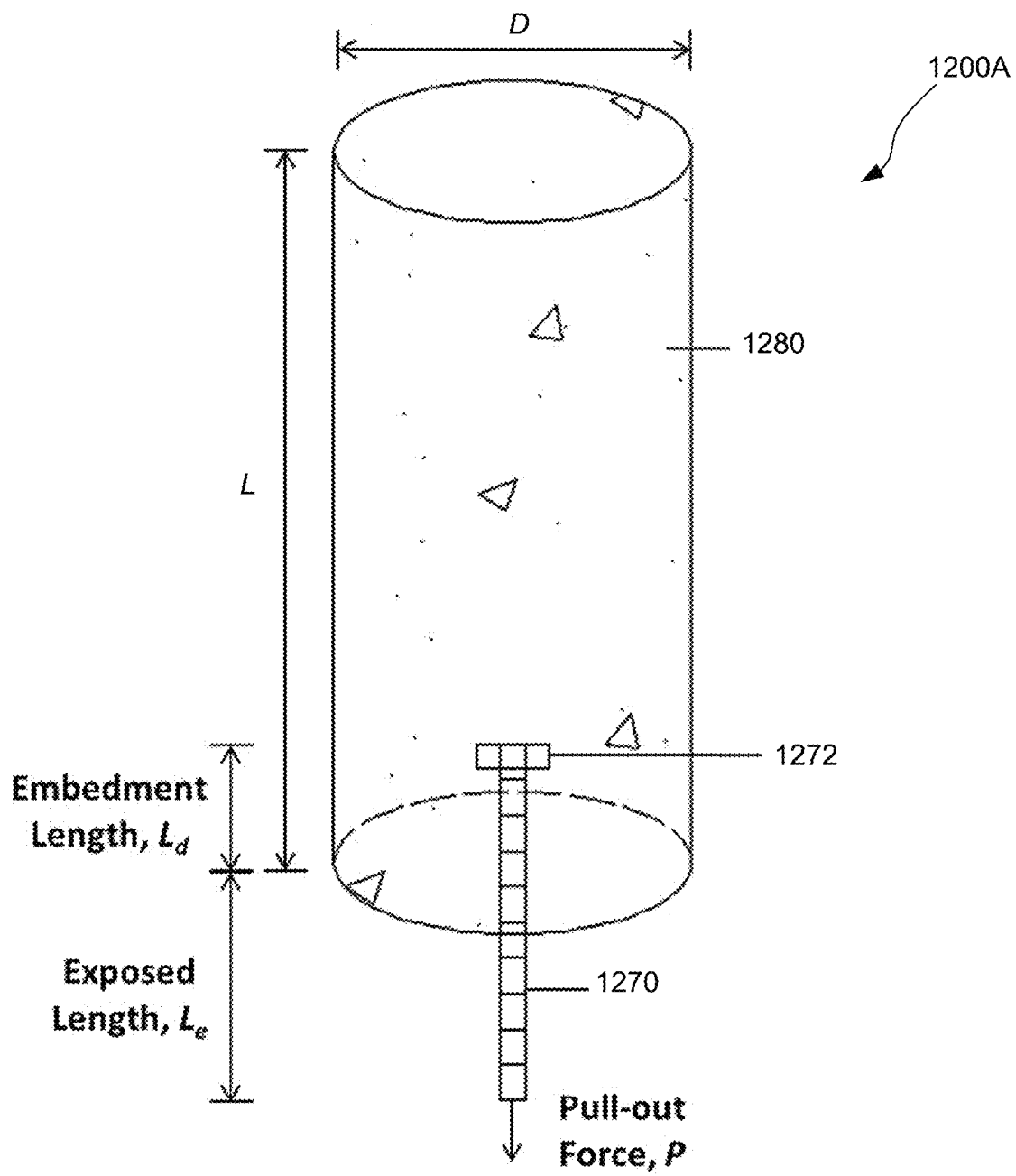
FIG. 12A is an exemplary schematic diagram showing anchor bolt installation and pullout testing according to certain embodiments.
Figure 12B:
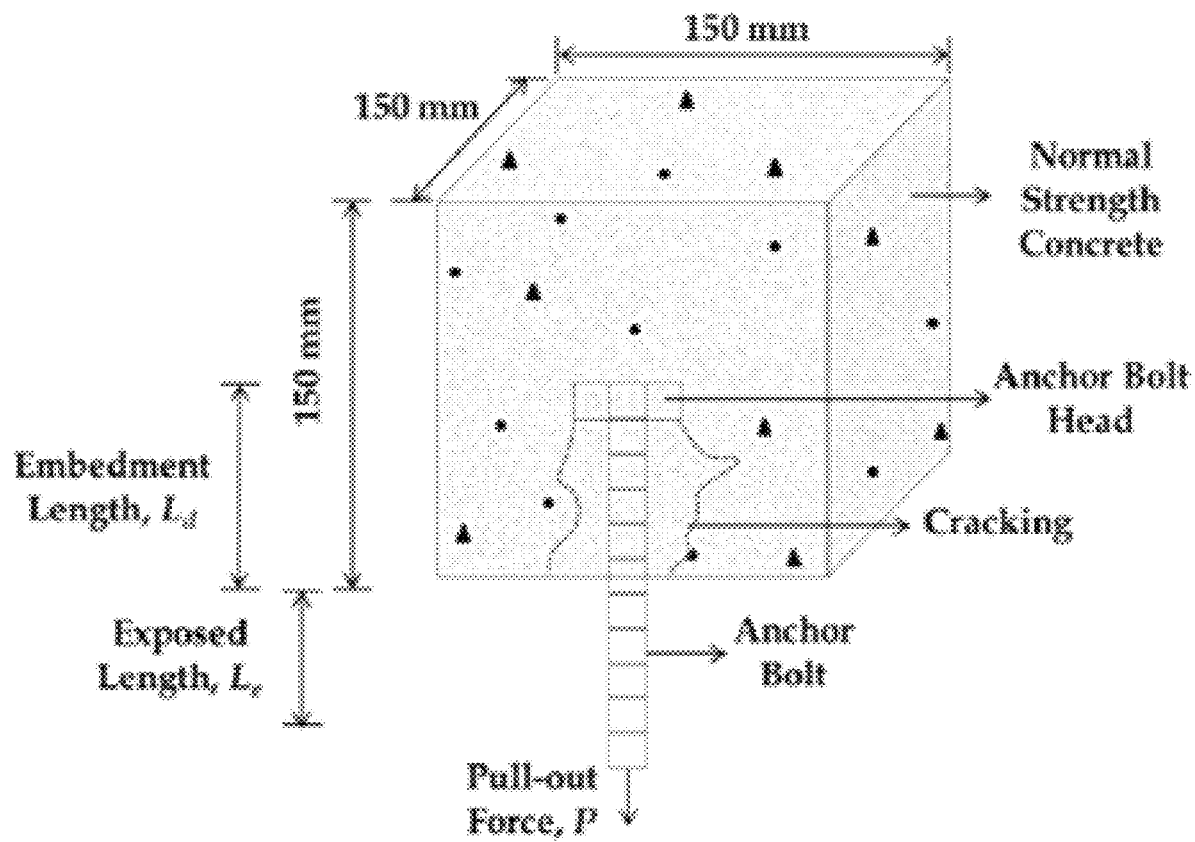
FIG. 12B is an exemplary schematic diagram showing anchor bolt installation and a vertical cracking pattern according to certain embodiments.
Figure 12C:
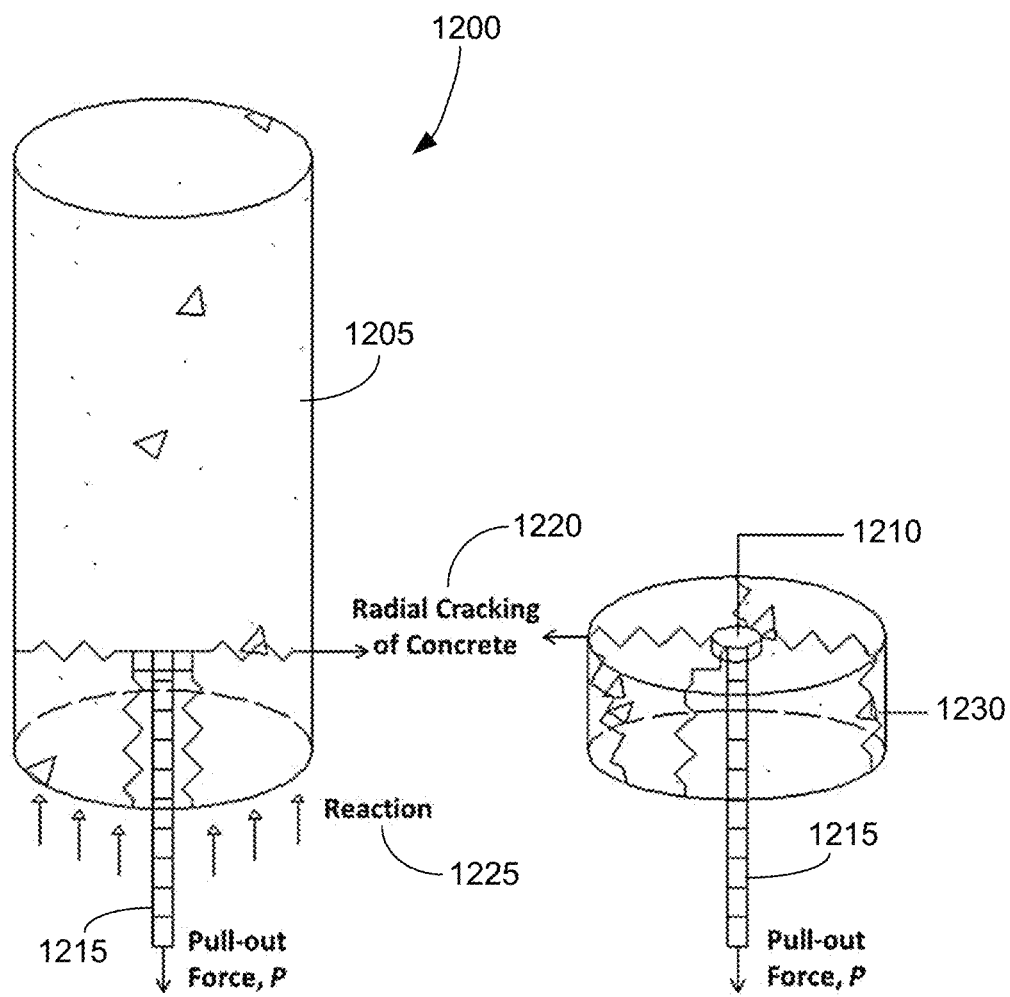
FIG. 12C is an exemplary schematic diagram showing anchor bolt installation and radial cracking pattern according to certain embodiments.
Figure 13:
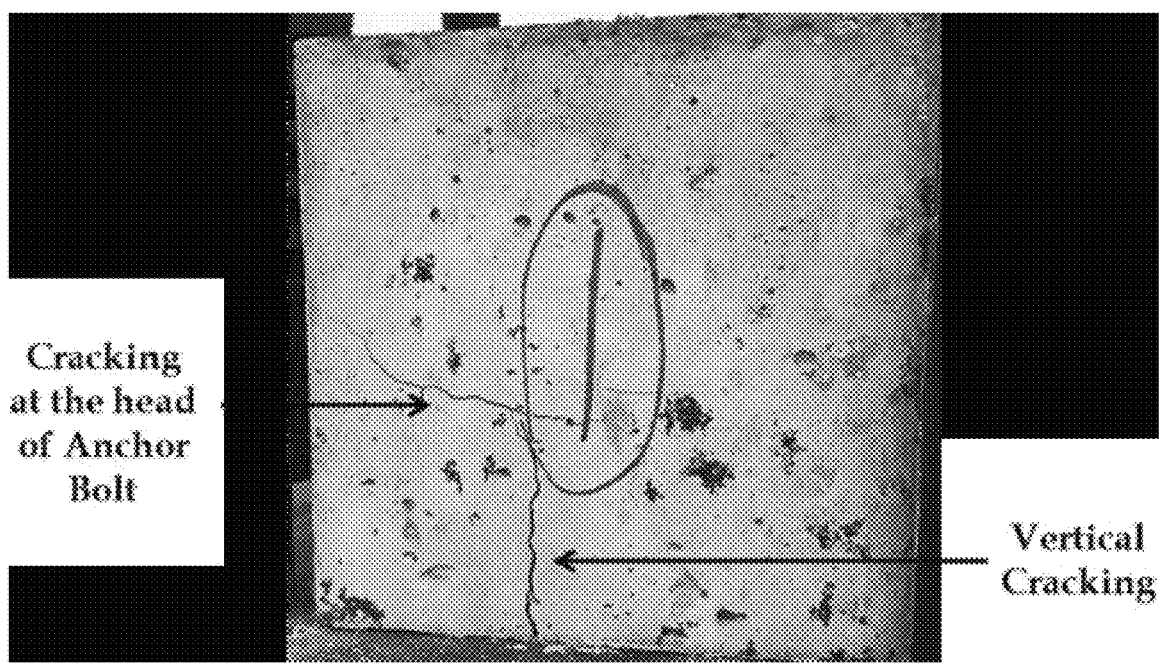
FIG. 13 is an illustration of vertical cracking along the anchor bolt embedment length.
Figure 14:
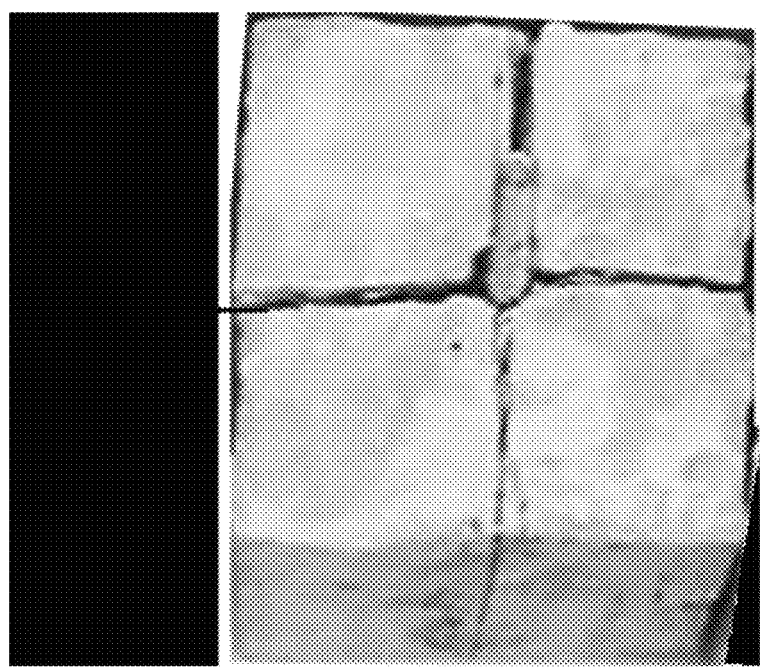
FIG. 14 is an illustration of cracking on top of the anchor bolt.

FIG. 12B and FIG. 12C depict a diagram of the internal stress distribution around an anchor bolt as represented by the cracking pattern. Traditional pullout tests lead to a cone type of failure however, owing to the reaction provided by the test setup, as shown in FIG. 12A, the anchor bolt experienced radial stress distribution resulting in circumferential crack propagation. A similar cracking pattern was observed during the testing as shown in FIG. 13 and FIG. 14 depicting a strong correlation between the conceptual theory and practical experimentation.

The bond between the steel anchor bolt and the surrounding concrete can be categorized into two main classes: a mechanical bond resulting from the interlocking between the bolt grooves and the surrounding concrete, and a frictional bond that occurs between the bolt and the cracked concrete surrounding the bolt. Upon initial loading, the mechanical bond is dominant and is responsible for the load carrying capacity, however, as the loading increases beyond the fracture strength, micro-cracks develop at the steel concrete interface. Upon a further increase in loading, these cracks bridge together to form large propagating vertical cracks as shown in FIG. 14, where the frictional bond is dominant. This process continues till the vertical cracks traverse the entire embedment length of the steel bolt. At this point in the loading all the mechanical bond along the length embedment length of the steel bolt has shifted from mechanical to frictional bond. The pullout process is then initiated, where upon further increase in loading the bolt is pulled out of the embedded concrete. At this stage the radial cracks appear as shown in FIG. 12C. The delay in the occurrence of radial cracking is due to the movement of the vertical cracks from the bottom of the anchor bolt towards the top. Finally, these vertical cracks result in the crushing of concrete leading to the eventual pullout of the embedded anchor bolt as shown in FIG. 13 and FIG. 14.

Results

Table 1 presents the values of Schmidt hammer rebound number corresponding to the pullout load strength. Table 2 presents the time taken by the ultrasonic pulse to travel 150 mm width of the cube specimen. The readings were adjusted for a correction factor related to a single steel bar embedded perpendicular to the path of wave propagation in a good quality concrete with the maximum aggregate size of 19 mm. Through the combined analysis of data presented in Table 1 and 2, the anchor bolts with poor quality of bond were identified. As mentioned above, anchor bolts with good quality of bond depict a higher rebound number as they are better able to transfer the impact energy to the surrounding concrete. Furthermore, well bonded anchor bolts depict a lower pulse velocity transit time, resulting in a faster ultrasonic pulse velocity. As a corollary, anchor bolts having porous bonds depict lower rebound numbers with larger variation among individual rebound readings and longer transit time resulting in a slower ultrasonic pulse transit velocity.

TABLE 1

Pull out strength and rebound readings for 12 mm φ bolt with embedment length of 50 mm.

| Bolt No. | Rebound Value (R) | | | | | Avg. (R) | Pull-Str. (KN) | Com. |
|---|---|---|---|---|---|---|---|---|
| | 1 | 2 | 3 | 4 | 5 | | | |
| 1 | 60 | 61 | 58 | 58 | 66 | 60.6 | 34.45 | |
| 2 | 52 | 66 | 49 | 64 | 65 | 59.2 | 30.54 | |
| 3 | 52 | 60 | 52 | 63 | 56 | 56.6 | 32.3 | ** IL |
| 4 | 42 | 50 | 50 | 44 | 44 | 46.0 | 27.6 | ** IL |
| 5 | 58 | 58 | 62 | 52 | 62 | 58.4 | 32.89 | |
| 6 | 52 | 54 | 55 | 58 | 61 | 56.0 | 31.47 | ** IL |
| 7 | 46 | 56 | 51 | 51 | 50 | 51.2 | 30.67 | |
| 8 | 60 | 50 | 58 | 56 | 52 | 55.2 | 32.28 | ** IL |
| 9 | 54 | 58 | 58 | 60 | 56 | 57.2 | 33.82 | |
| 10 | 59 | 54 | 57 | 58 | 54 | 56.4 | 33.48 | |
| 11 | 60 | 50 | 63 | 49 | 64 | 57.2 | 38.55 | |
| 11 | 62 | 64 | 62 | 62 | 65 | 63.0 | 36.05 | |
| 13 | 58 | 50 | 54 | 58 | 50 | 54.0 | 31.88 | |
| 14 | 60 | 63 | 65 | 65 | 66 | 63.8 | 37.44 | |
| 15 | 60 | 66 | 62 | 58 | 56 | 60.4 | 35.4 | ** IL |
| 16 | 58 | 50 | 61 | 53 | 52 | 55.0 | 35.15 | |
| 17 | 65 | 43 | 60 | 56 | 68 | 58.4 | 36.97 | |
| 18 | 58 | 61 | 60 | 61 | 58 | 59.6 | 34.5 | ** IL |
| 19 | 58 | 52 | 54 | 56 | 52 | 54.3 | 33.31 | |
| 20 | 63 | 56 | 57 | 60 | 49 | 57.0 | 32.89 | |

** IL - Non-vertical anchor bolts with ill-alignment less than 10° & porous quality of bond between concrete and bolt.

TABLE 2

Ultrasonic Pulse Velocity reading for 12 mm φ bolt with embedment length of 50 mm and 70 mm.

| Bolt No. | 50 mm | | | 75 mm | | |
|---|---|---|---|---|---|---|
| | Avg. Time (μs) | Avg. Vel. (m/s) | Co. | Avg. Time (μs) | Avg. Vel. (m/s) | Co. |
| 1 | 31.32 | 4788.59 | | 30.24 | 4.960.11 | |
| 2 | 30.89 | 4855.78 | | 31.07 | 4528.33 | |
| 3 | 31.63 | 4741.78 | ** | 30.90 | 4854.78 | |
| 4 | 31.39 | 4718.33 | ** | 30.81 | 4868.56 | ** |
| 5 | 31.39 | 4775.44 | | 30.61 | 4900.22. | |
| 6 | 31.80 | 4716.98 | ** | 30.53 | 4912.44 | |
| 7 | 31.39 | 4779.33 | | 30.93 | 4848.89 | |
| 8 | 31.73 | 4727.00 | ** | 31.01 | 4837.78 | |
| 9 | 31.40 | 4777.67 | | 30.90 | 4854.00 | |
| 10 | 31.53 | 4756.59 | | 31.00 | 4838.89 | |
| 11 | 30.97 | 4843.56 | | 31.10 | 4824.00 | ** |
| 12 | 31.41 | 4775.22. | | 30.64 | 4896.11 | ** |
| 13 | 31.50 | 4761.90 | | 31.32 | 4788.00 | |
| 14 | 31.49 | 4764.00 | | 30.90 | 4856.67 | ** |
| 15 | 31.74 | 4725.89 | ** | 31.09 | 4826.44 | ** |
| 16 | 31.39 | 4779.27 | | 30.69 | 4887.78 | |
| 17 | 31.32 | 4790.22. | | 30.76 | 4877.11 | |
| 18 | 31.70 | 4732.44 | ** | 30.50 | 4917.89 | |
| 19 | 31.31 | 4790.44 | | 30.73 | 4880.67 | ** |
| 70 | 30.88 | 4858.56 | | 30.77 | 4875.44 | ** |

** Slower ultrasonic pulse velocity transit time result in lower pulse transit time.

Figure 15:
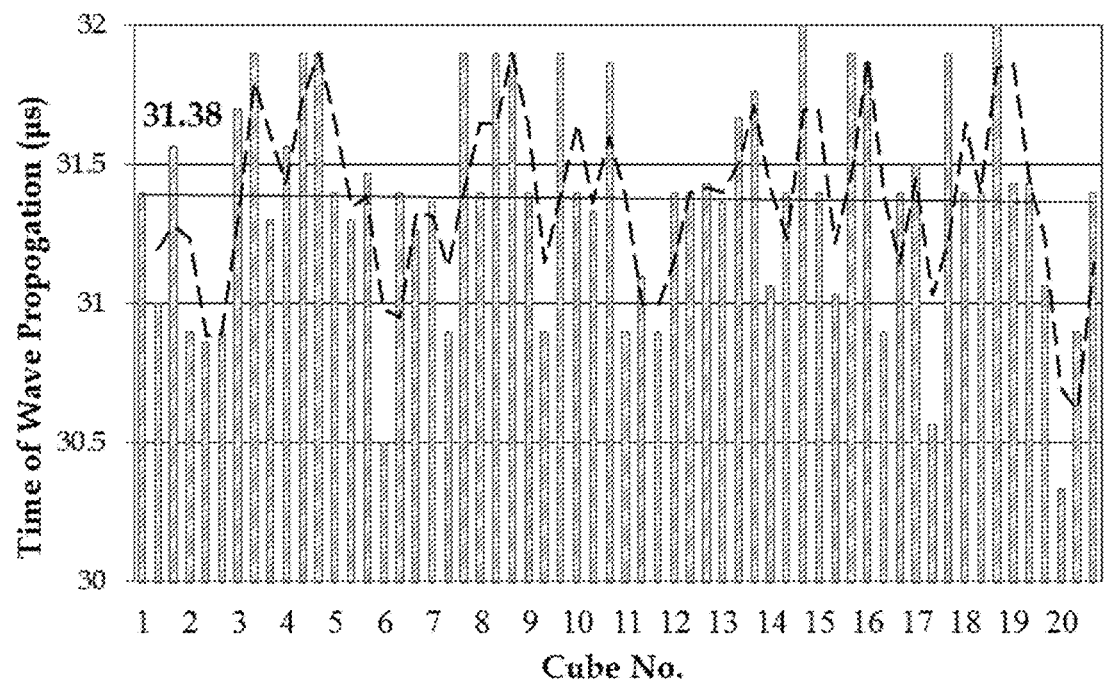
FIG. 15 is a graph of variation in ultrasonic pulse velocity along the embedment depth of anchor bolt for 12 mm Φ anchor bolt with embedment length of 50 mm.

FIG. 15 presents the variation in ultrasonic pulse velocity along the depth of the 12 mm Φ diameter anchor bolt with 50 mm embedment length. The data presented in the figure is for three location along the depth of the anchor bolts, where each location rep-resents the average of three readings. From the analysis of the presented result is was noticed that cube specimens number 3, 4, 6, 8, 15 and 18 depict higher ultrasonic wave transit time.

Furthermore, the analysis of data presented in Table 1 shows that these specimens also depict a large variation in rebound value. One important observation during the testing was that the UPV reading close to the surface of the cube results in the slowest time. This phenomenon can be attributed by improper compaction of the surface layer of concrete since majority of water and air bubbles are present near the concrete surface.

The results from Tables 1 and 2 and FIG. 15 reveal that anchor bolts having a slower wave propagation also have a lower Schmidt hammer rebound number. These two sets of indicators can be used to identify anchor bolts with lower pullout load capacity.

Figure 16:
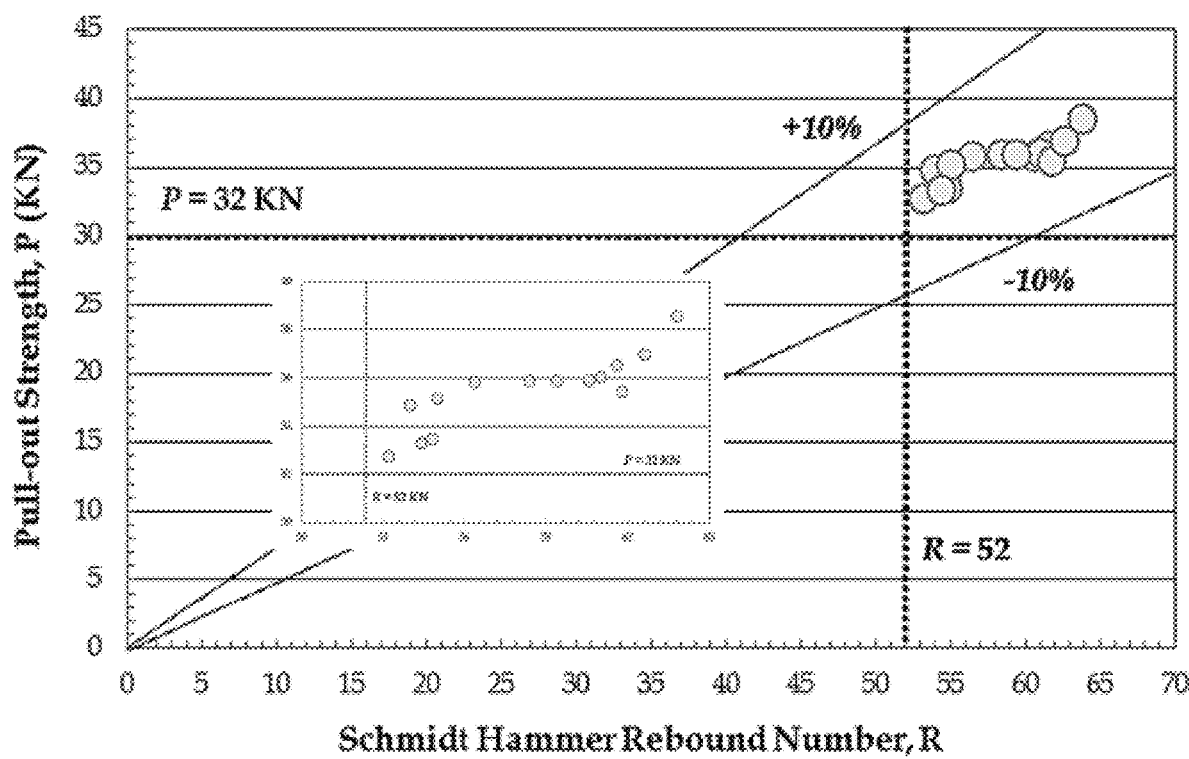
FIG. 16 is a graph of pullout load versus rebound number relationship for 12 mm anchor bolt with embedment length of 50 mm.

FIG. 16 is a graph of pullout load capacity versus Schmidt hammer rebound number. As the Schmidt hammer rebound number, R, increases, the pullout loading carrying capacity, P, also increases. In the rebound number range from 50 to the peak value near 65, the bolts situated at the lower spectrum represent the bolts with slightly poor alignment, 0-15 degrees off vertical, more typically 5-8 degrees off vertical. Analysis of the data also reveals that faulty bolts depict a much lower pullout load capacity and hence were ignored in the data presented in FIG. 16. Thus the conclusion can be drawn that it is to possible to identify anchor bolts with lower pullout load capacity by combining the UPV test readings with the Schmidt hammer rebound number. Furthermore, the Schmidt hammer rebound number, R equal to 52, can be treated as cutoff number below which anchor bolts with 12 mm Φ having an embedment length of 50 mm cannot be relied upon for large load carrying capacity.

Figure 17:
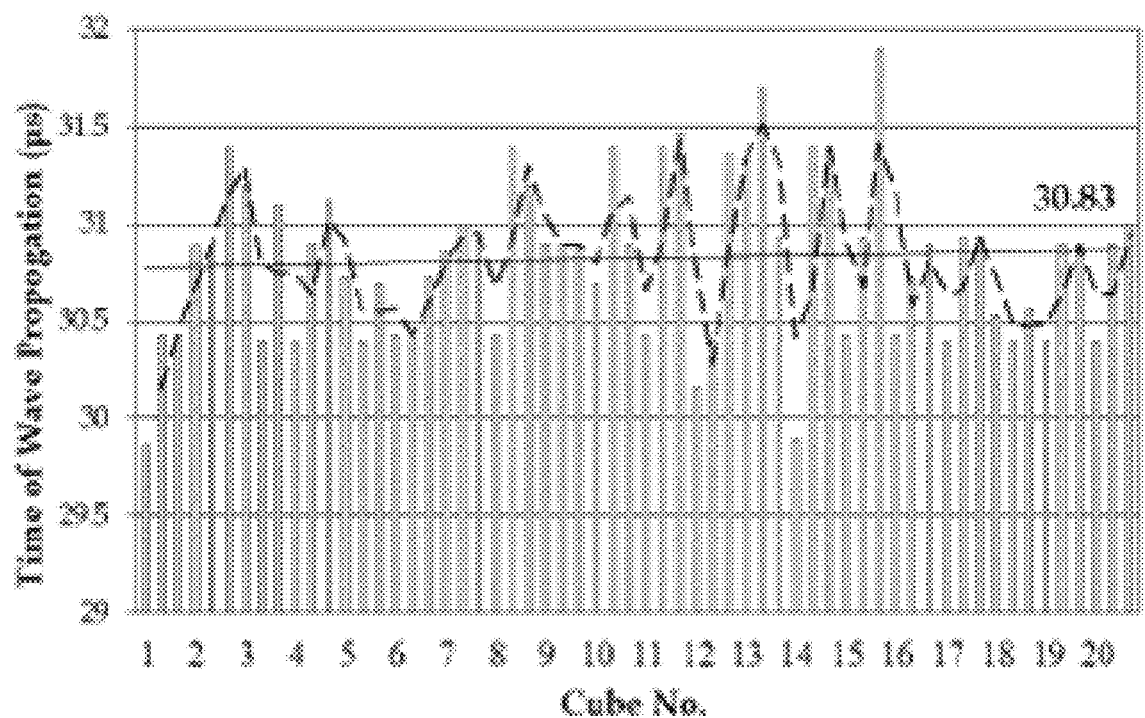
FIG. 17 is a graph of variation in ultrasonic pulse velocity along the embedment depth of anchor bolt for 12 mm Φ anchor bolt with embedment length of 70 mm.

Table 3 presents the result of Schmidt hammer rebound testing for 12 mm Φ bolts with 70 mm embedment length. Table 2 and FIG. 17 present the results of ultrasonic pulse velocity testing for the same anchor bolts. From the analysis of results presented in the Tables 2, 3 and FIG. 17, seven faulty anchor bolts were identified which resulted in lower pullout load capacity.

TABLE 3

Pullout strength and rebound readings for 12 mm Φ bolt with embedment length of 70 mm.

| Bolt No. | Rebound Value (R) | | | | | Avg. (R) | Pull-Str. (KN) | Com. |
|---|---|---|---|---|---|---|---|---|
| | 1 | 2 | 3 | 4 | 5 | | | |
| 1 | 44 | 56 | 60 | 58 | 62 | 56.0 | 47.97 | |
| 2 | 55 | 62 | 62 | 60 | 60 | 59.8 | 49.87 | |
| 3 | 58 | 60 | 58 | 63 | 48 | 57.4 | 51.66 | |
| 4 | 42 | 40 | 50 | 60 | 62 | 50.8 | 45.12 | ** IL |
| 5 | 53 | 60 | 64 | 66 | 61 | 60.8 | 50.34 | |
| 6 | 52 | 65 | 65 | 64 | 63 | 61.8 | 51.94 | |
| 7 | 58 | 64 | 55 | 61 | 60 | 59.6 | 49.07 | |
| 8 | 55 | 60 | 58 | 60 | 59 | 58.4 | 50.83 | |
| 9 | 57 | 62 | 64 | 62 | 67 | 62.4 | 52.85 | |
| 10 | 55 | 62 | 62 | 64 | 64 | 61.4 | 49.86 | |
| 11 | 60 | 52 | 58 | 63 | 65 | 59.6 | 58.64 | ** IL |
| 12 | 62 | 62 | 62 | 58 | 62 | 61.2 | 46.5 | ** IL |
| 13 | 55 | 58 | 60 | 58 | 60 | 58.2 | 49.72 | |
| 14 | 60 | 65 | 66 | 65 | 68 | 64.8 | 45.63 | ** IL |
| 15 | 58 | 63 | 64 | 65 | 65 | 63.0 | 39.92 | ** IL |
| 16 | 60 | 60 | 62 | 59 | 64 | 61.0 | 49.67 | |
| 17 | 58 | 58 | 6' | 61 | 54 | 58.8 | 50.92 | |
| 18 | 54 | 63 | 67 | 66 | 65 | 63.0 | 52.76 | |
| 19 | 61 | 64 | 67 | 58 | 66 | 62.4 | 47.97 | ** IL |
| 20 | 54 | 61 | 64 | 66 | 63 | 61.6 | 44.81 | ** IL |

** IL - Non-vertical anchor bolts with ill-alignment less than 10° & porous quality of bond between concrete and bolt.

The methodology involved in identifying faulty anchor bolts is based on the rationale, as presented above with respect to FIG. 11, that ultrasonic pulse velocity is greater in the solid medium as compared to a porous medium, furthermore the ultrasonic pulse travels faster through the steel anchor bolt as compared to the concrete. Thus by testing the ultrasonic pulse transit time perpendicular to the anchor bolt embedment length the researcher can identify bond quality of anchor bolt. Since the anchor bolts with good bond quality exhibit faster wave transmit time as compared to anchor bolts with porous bonds, the data can be used to pinpoint anchor bolts with poor bond quality. As anchor bolts with lower pullout load capacity exhibit lower rebound number, relating the UPV test results to the lower average Schmidt hammer rebound number identifies the faulty anchor bolts.

FIG. 17 presents the UPV test results for anchor bolts with 70 mm embedment depth. Three locations were selected along the embedment depth as shown in the FIG. 5A and three readings of the time of wave propagation were taken at each location (cube number) and averaged. Bolt numbers 4, 11, 12, 15, 16, 19 and 20 all have the UPV readings above the mean average value of 30.83 μs. This indicates that the bond quality for these bolt elements is porous (cracked, pores formed, water pockets, etc.) since the ultrasonic pulse wave takes a longer time to transit the same path length. For several bolt elements the UPV readings near the surface are slower, which is an erroneous reading due to the presence of air bubbles near the surface layer, which is responsible for the transit time delay of the ultrasonic pulse.

Table 3 depicts the pullout load capacity versus the Schmidt hammer rebound number. It can be noticed that for anchor bolt numbers 4, 11, 12, 15, 16, 19 and 20, there exists a large variation in the Schmidt hammer rebound number, which verifies the findings of the UPV testing.

Figure 18:
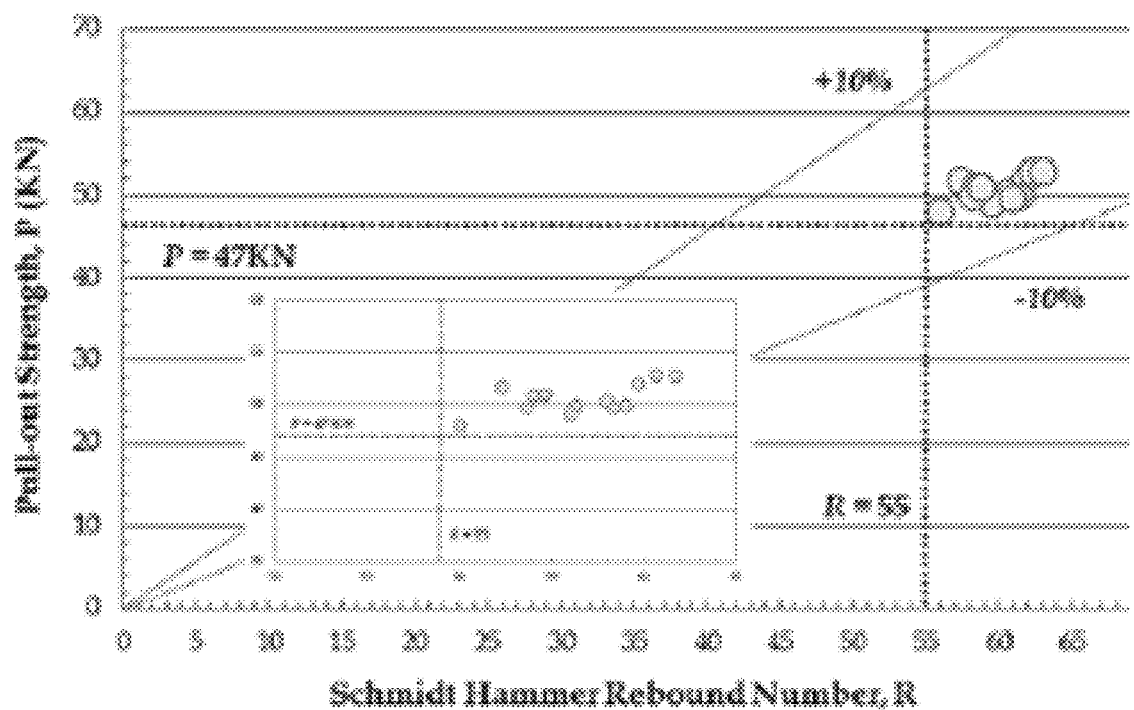
FIG. 18 is a graph of pullout load versus rebound number relationship for 12 mm Φ anchor bolt with embedment length of 70 mm.

From FIG. 18 it can be seen that there exists a clear cut-off rebound number, R equals 55, for which a minimum of pullout load capacity of 47 KN can be achieved. Hence, it can be said that rebound number of 55 can be treated as a cut-off below which bolts with 12 mm Φ bolt having an embedment length of 70 mm cannot be relied upon for large load carrying capacity.

Figure 19:
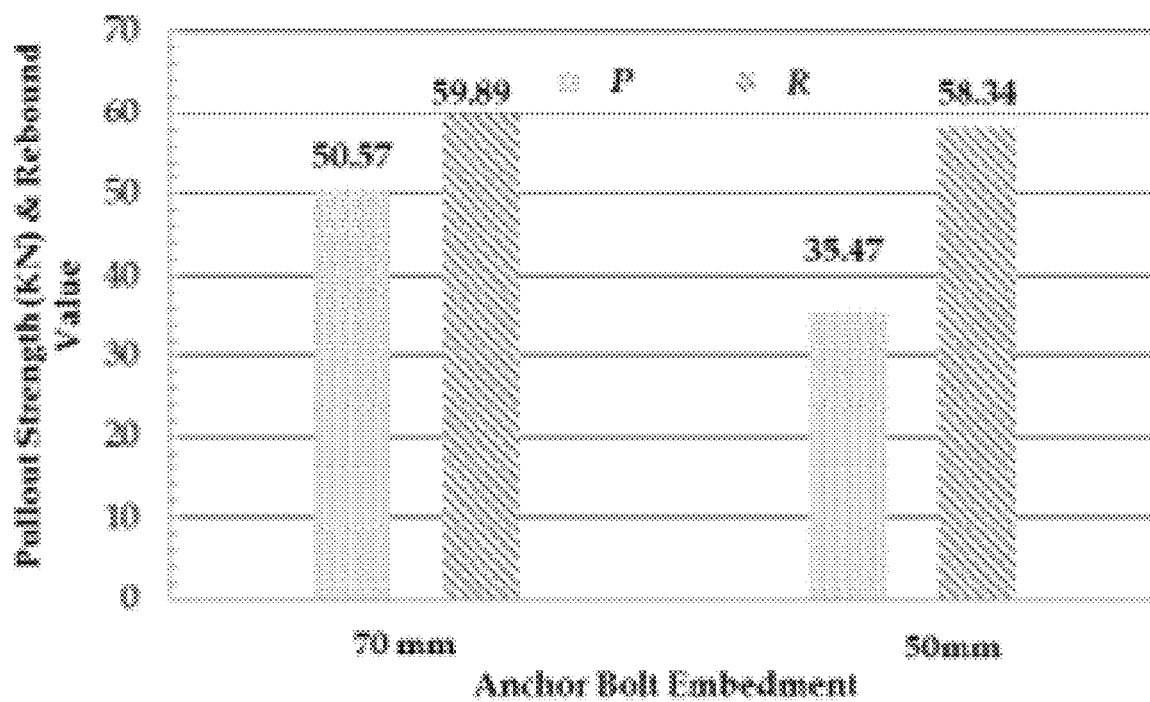
FIG. 19 is a histogram of average pullout load versus rebound number comparison for 12 mm Φ anchor bolt.

FIG. 19 is a graph of average pullout load capacity and average rebound number for 70 mm and 5 mm length bolts. It can be seen that although the average rebound number R is almost the same for anchor bolt with 50 mm and 70 mm embedment length, the corresponding pullout load capacity for the 70 mm embedment length anchor bolts is 29.9% higher than for the 50 mm embedment length bolts. Hence, it can be concluded that for equal anchor bolt diameter, the pullout load capacity for the longer embedment length is greater than the pullout load capacity for the shorter embedment length.

Figure 20:
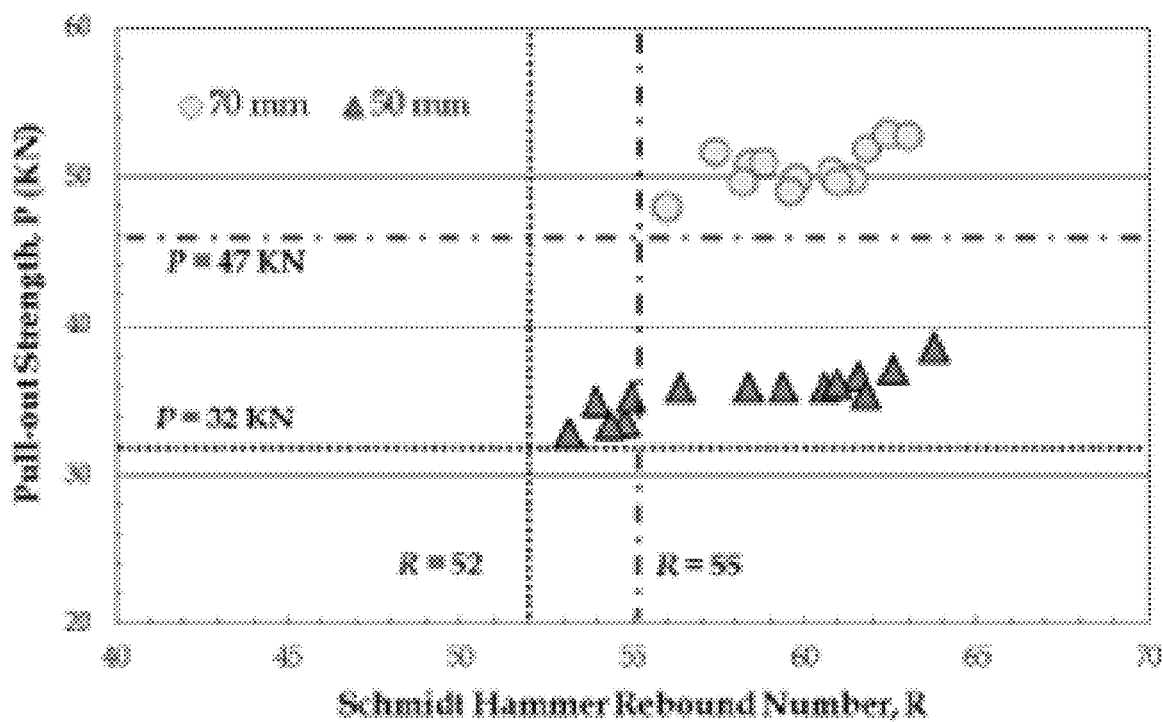
FIG. 20 is a graph of combined pullout load capacity versus Schmidt hammer rebound number.

FIG. 20 demonstrates the combined pullout load capacity versus the Schmidt hammer rebound number. The results show that there is a clear range of rebound numbers for 50 mm embedment length and 70 mm embedment length. Anchor bolts with poor alignment, porous bond and improper embedment depth can be identified using the rebound number as they depict a rebound number below the specified cut-off value. Furthermore, as the embedment depth increases the load carrying capacity increases. In addition, the UPV test acts as an confirmation tool to identify anchor bolts with poor installation.

The discussion above demonstrates the improvement gained in identifying anchor bolts with poor bond quality and reduced pullout load capacity by combining ultrasonic pulse velocity testing with Schmidt hammer rebound testing. The following observations derive from the present disclosure:

1. Ultrasonic pulse velocity testing combined with Schmidt hammer testing can be used to successfully identify faulty anchor bolts having poor bonds to the concrete, such as cracking, air pockets and pore formation. Anchor bolts with poor bonds exhibit lower rebound number, R, and a longer ultrasonic pulse transit time, as shown by Saleem et al. ("Study to detect bond degradation in reinforced concrete beams using ultrasonic pulse velocity test method", Structural Engineering and Mechanics, July, 2017), incorporated herein by reference in its entirety. 2. Anchor bolts with poor alignment and poor bonds cannot be relied upon to have higher pullout load capacity, possibly causing failure of the attachment. Using the combination of the UPV and Schmidt hammer rebound number non-destructive testing method shown above, it is possible to pinpoint anchor bolts with reduced pullout load capacity.

3. In some embodiments rebound numbers, i.e. R of 52 for 32 KN pullout load capacity and 55 for 47 KN pullout load capacity, can be treated as a cut-off values for anchor bolts of 12 mm Φ with embedment length of 50 mm and 70 mm, respectively. Anchor bolts which display rebound numbers lower than the specified values cannot be relied upon for large load carrying capacity.

The present disclosure describes the use of an ultrasonic pulse velocity test combined with a Schmidt hammer rebound test to identify faulty anchor bolts.

Combining the UPV test with the Schmidt hammer test as detailed in the present disclosure enables a user to identify anchor bolts with improper installation, poor alignment, porous bond or anchor bolts with improper embedment. The non-destructive investigation results in increased efficiency and accuracy of field measurements.

Figure 21:
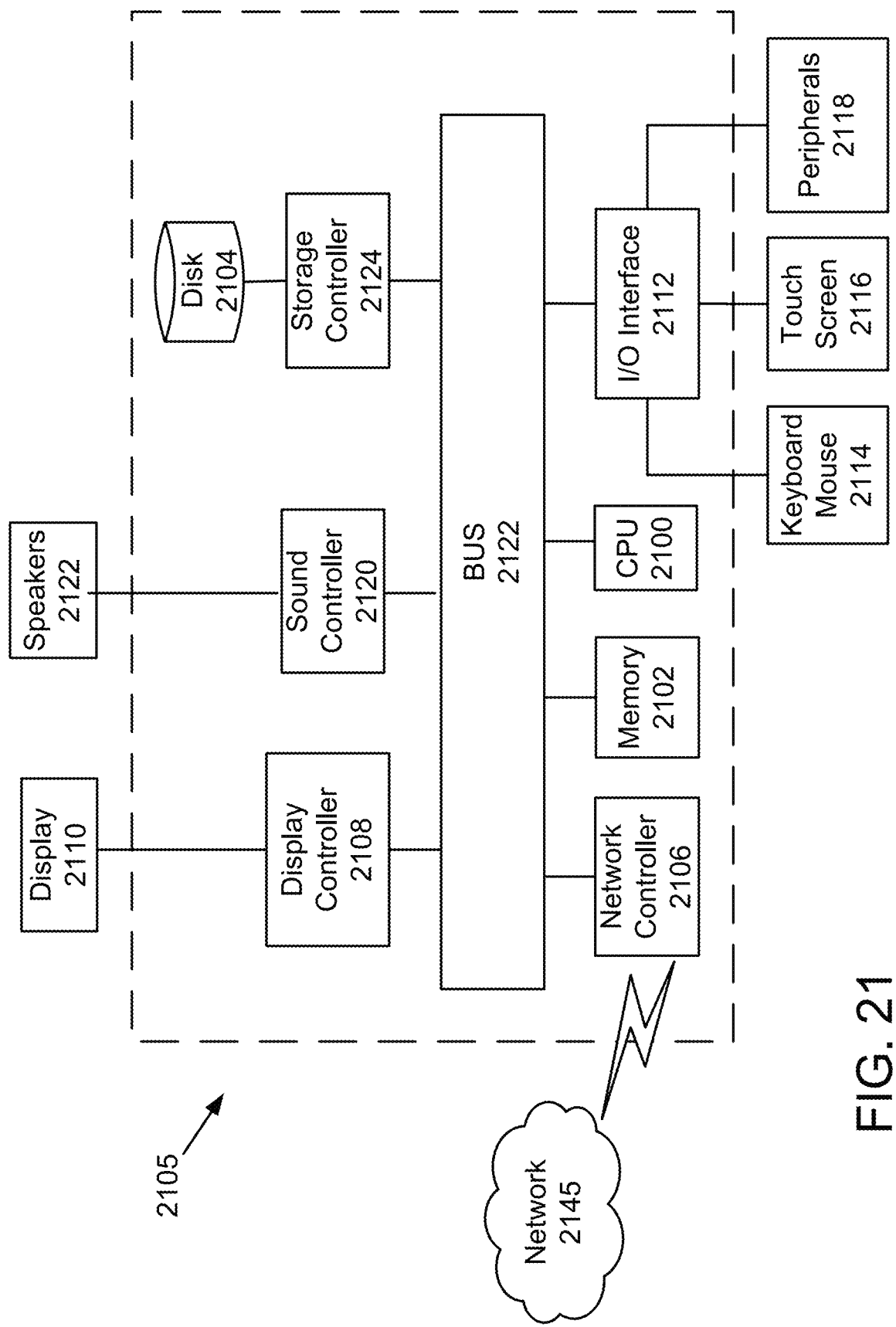
FIG. 21 shows distributed components including one or more client and server machines, which may share processing.

Next, a hardware description of the controllers according to exemplary embodiments is described with reference to FIG. 21. In FIG. 21, the controller described is representative of the controller 305 of FIG. 3, the Schmidt hammer control strip 253 as shown in FIG. 2 or UPV controller 550 of FIG. 5B in which the controller is a computing device which includes a CPU 2100 which performs the processes described above/below. The process data and instructions may be stored in memory 2102. These processes and instructions may also be stored on a storage medium disk 2104 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claimed advancements may be provided as a utility application, background daemon, or component of an operating system, or combination thereof, executing in conjunction with CPU 2100 and an operating system such as Microsoft Windows 7, UNIT, Solaris, LINUX7, Apple MAC-OS and other systems known to those skilled in the art.

The hardware elements in order to achieve the computing device may be realized by various circuitry elements, known to those skilled in the art. For example, CPU 2100 may be a Xenon or Core processor from Intel of America or an Opteron processor from AMD of America, or may be other processor types that would be recognized by one of ordinary skill in the art. Alternatively, the CPU 2100 may be implemented on an FPGA, ASIC, PLD or using discrete logic circuits, as one of ordinary skill in the art would recognize. Further, CPU 2100 may be implemented as multiple processors cooperatively working in parallel to perform the instructions of the inventive processes described above.

The computing device in FIG. 21 also includes a network controller 2106, such as an Intel Ethernet PRO network interface card from Intel Corporation of America, for interfacing with network 2145. As can be appreciated, the network 2145 can be a public network, such as the Internet, or a private network such as an LAN or WAN network, or any combination thereof and can also include PSTN or ISDN sub-networks. The network 2145 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 2108, such as a NVIDIA GeForce GT21 or Quadro graphics adaptor from NVIDIA Corporation of America for interfacing with display 2110, such as a Hewlett Packard HPL2445w LCD monitor. A general purpose I/O interface 2112 interfaces with a keyboard and/or mouse 2114 as well as a touch screen panel 2116 on or separate from display 2110. General purpose I/O interface also connects to a variety of peripherals 2118 including printers and scanners, such as an OfficeJet or DeskJet from Hewlett Packard. A sound controller 2120 is also provided in the computing device such as Sound Blaster 21-Fi Titanium from Creative, to interface with speakers/microphone 2122 thereby providing sounds and/or music.

The general purpose storage controller 2124 connects the storage medium disk 2104 with communication bus 2126, which may be an ISA, EISA, VESA, PCI, or similar, for interconnecting all of the components of the computing device. A description of the general features and functionality of the display 2110, keyboard and/or mouse 2114, as well as the display controller 2108, storage controller 2124, network controller 2106, sound controller 2120, and general purpose I/O interface 2112 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 22.

Figure 22:
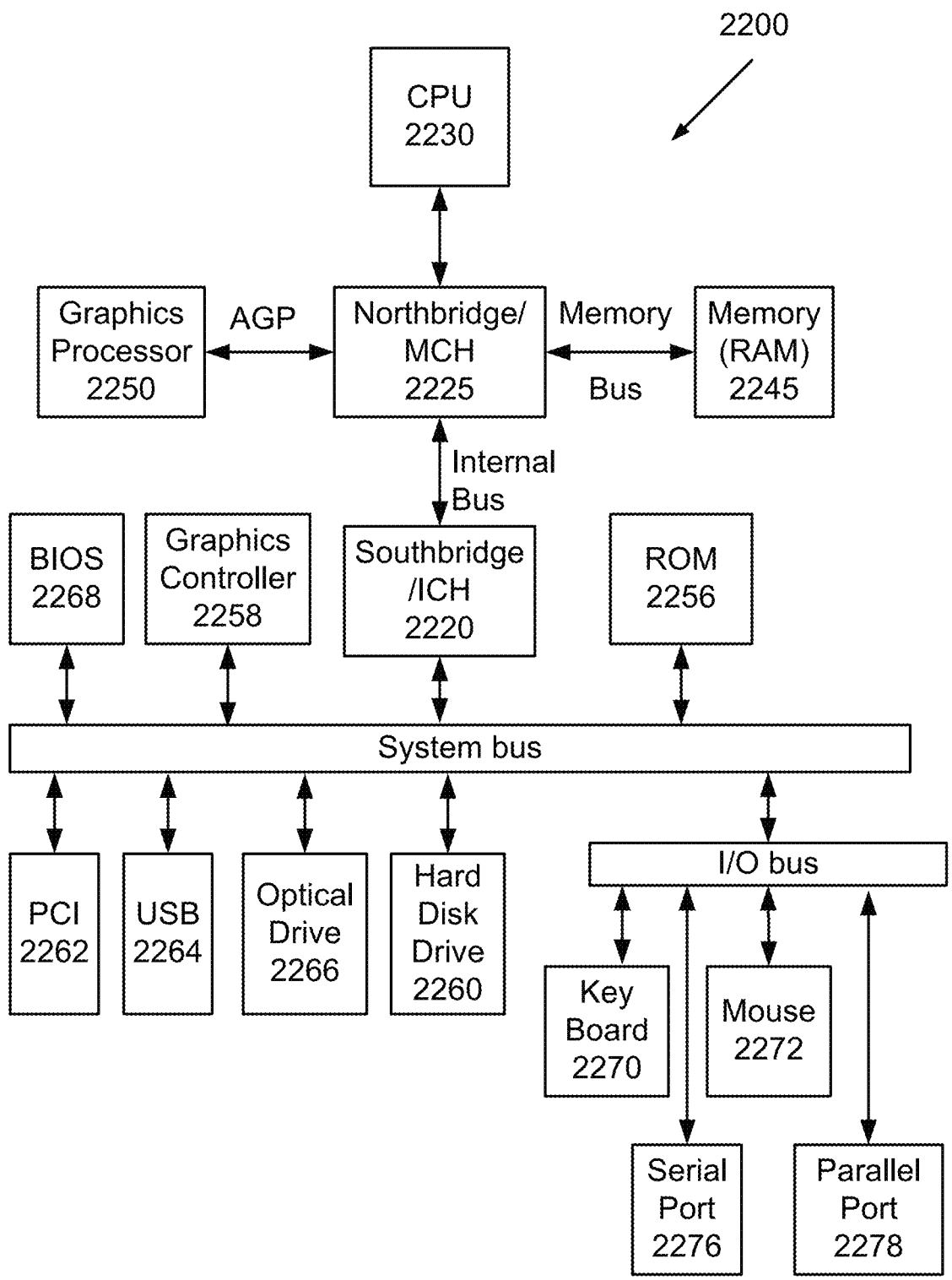
FIG. 22 shows hardware for the computing device used in the exemplary embodiments.

FIG. 22 shows a schematic diagram of a data processing system, according to certain embodiments, for performing the functions of the exemplary embodiments. The data processing system is an example of a computer in which code or instructions implementing the processes of the illustrative embodiments may be located.

In FIG. 22, data processing system 2200 employs a hub architecture including a north bridge and memory controller hub (NB/MCH) 2225 and a south bridge and input/output (I/O) controller hub (SB/ICH) 2220. The central processing unit (CPU) 2230 is connected to NB/MCH 2225. The NB/MCH 2225 also connects to the memory 2245 via a memory bus, and connects to the graphics processor 2250 via an accelerated graphics port (AGP). The NB/MCH 2225 also connects to the SB/ICH 2220 via an internal bus (e.g., a unified media interface or a direct media interface). The CPU Processing unit 2230 may contain one or more processors and even may be implemented using one or more heterogeneous processor systems.

Figure 23:
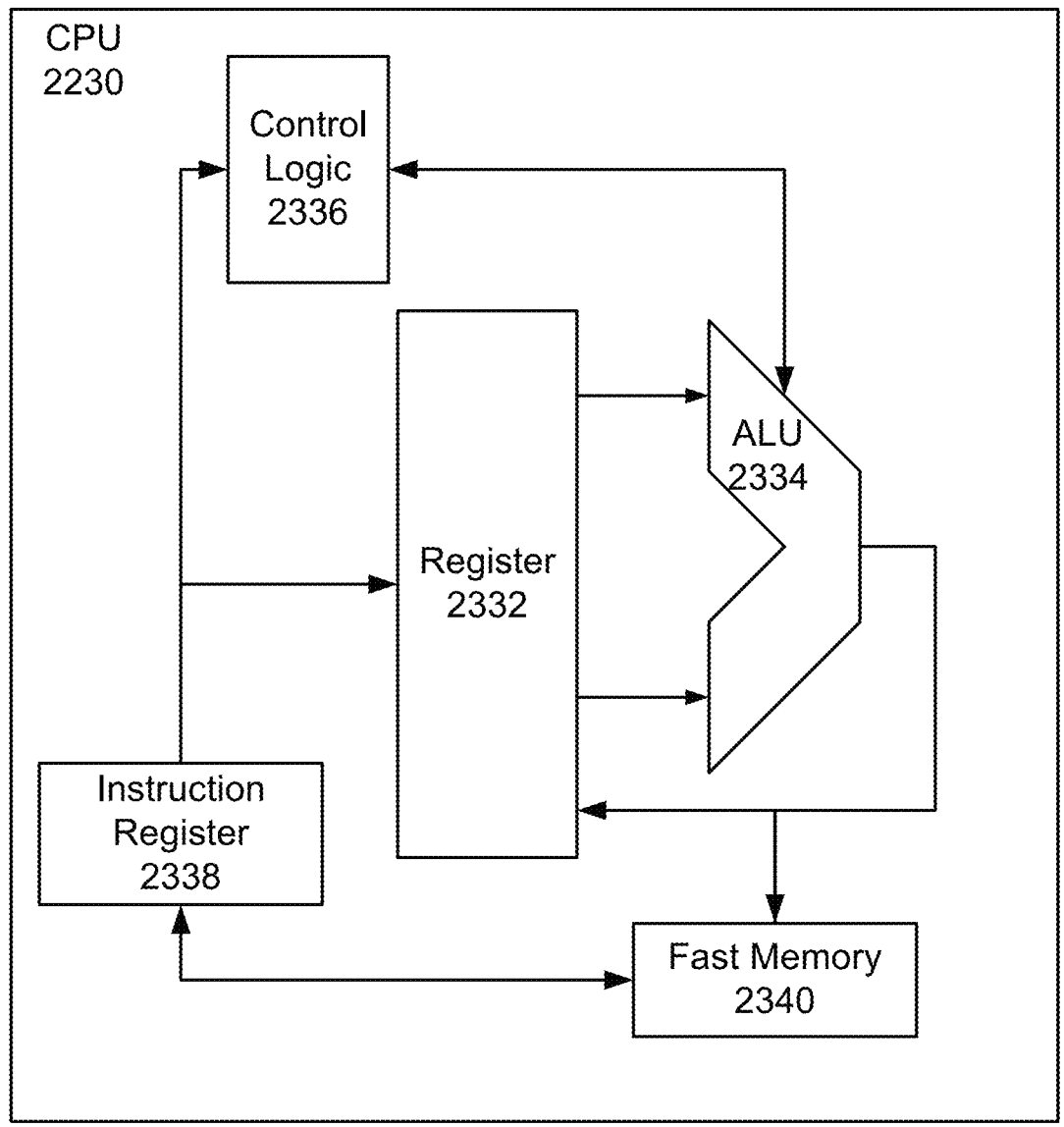
FIG. 23 shows circuitry configured to perform features of the invention.

For example, FIG. 23 shows one implementation of CPU 2230. In one implementation, the instruction register 2338 retrieves instructions from the fast memory 2340. At least part of these instructions are fetched from the instruction register 2338 by the control logic 2336 and interpreted according to the instruction set architecture of the CPU 830. Part of the instructions can also be directed to the register 2332. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 2334 that loads values from the register 2332 and performs logical and mathematical operations on the loaded values according to the instructions. The results from these operations can be feedback into the register and/or stored in the fast memory 2340. According to certain implementations, the instruction set architecture of the CPU 2230 can use a reduced instruction set architecture, a complex instruction set architecture, a vector processor architecture, a very large instruction word architecture. Furthermore, the CPU 2230 can be based on the Von Neuman model or the Harvard model. The CPU 2230 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 22, the data processing system 2200 can include that the SB/ICH 2220 is coupled through a system bus to an I/O Bus, a read only memory (ROM) 2256, universal serial bus (USB) port 2264, a flash binary input/output system (BIOS) 2268, and a graphics controller 2258. PCI/PCIe devices can also be coupled to SB/ICH 2220 through a PCI bus 2262.

The PCI devices may include, for example, Ethernet adapters, add-in cards, and PC cards for notebook computers. The Hard disk drive 2260 and CD-ROM 2266 can use, for example, an integrated drive electronics (IDE) or serial advanced technology attachment (SATA) interface. In one implementation the I/O bus can include a super I/O (SIO) device.

Further, the hard disk drive (HDD) 2260 and optical drive 2266 can also be coupled to the SB/ICH 2220 through a system bus. In one implementation, a keyboard 2270, a mouse 2272, a parallel port 2278, and a serial port 2276 can be connected to the system bus through the I/O bus. Other peripherals and devices that can be connected to the SB/ICH 2220 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 24:
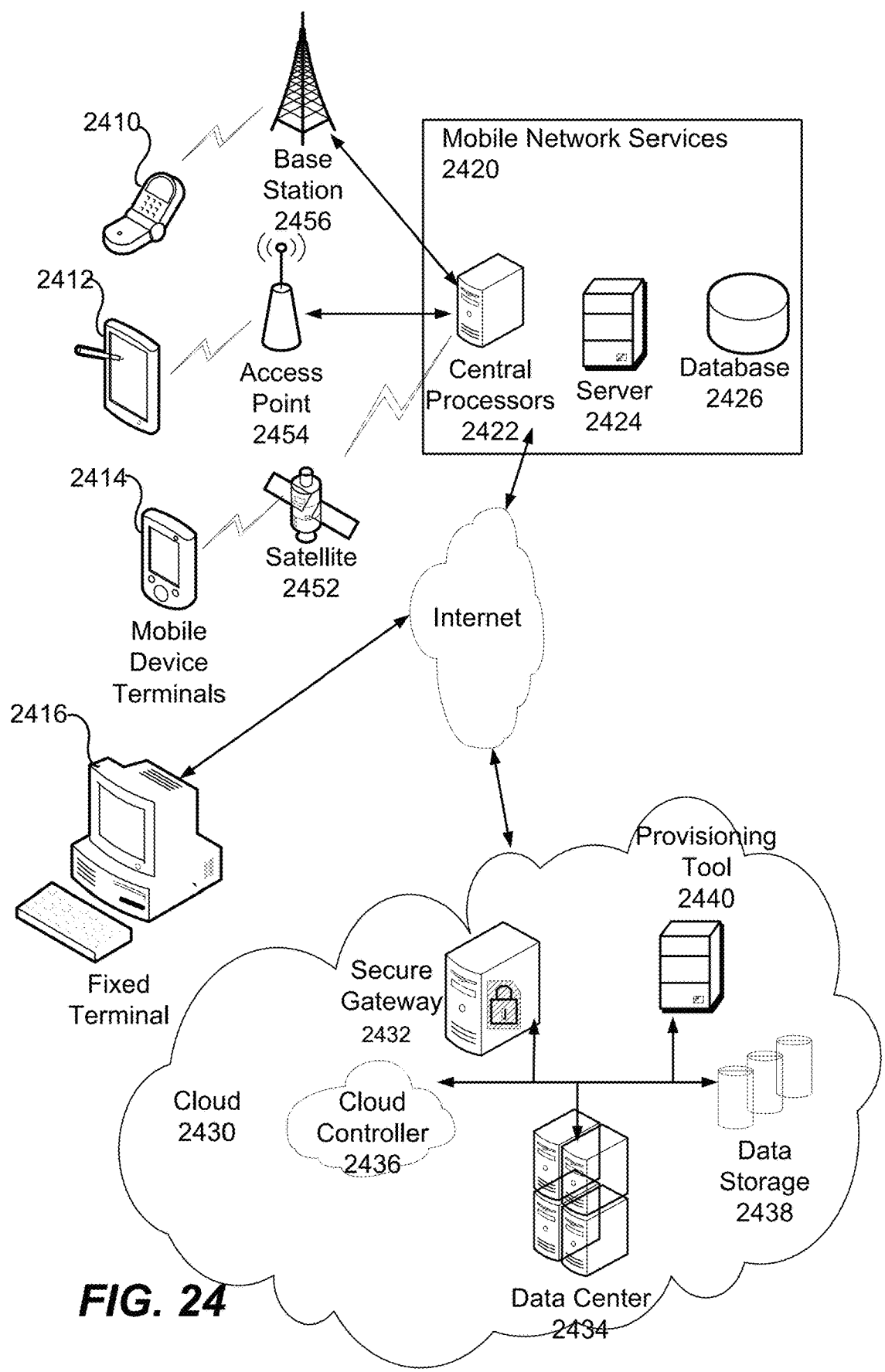
FIG. 24 shows a data processing system hub used in the exemplary embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 24, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present invention are possible in light of the above teachings. It is therefore to be understood that within the scope of the appended claims, the invention may be practiced otherwise than as specifically described herein.

Abbreviation

R=Schmidt Hammer Rebound Number
P=Pullout Load Carrying Capacity
IL=ill-aligned Anchor Bolt
Ld=Embedment Length
Le=Exposed Length
LT=Total Length of Anchor Bolt

The invention claimed is:

1. An anchor bolt pull out load capacity testing system, comprising:
    a Schmidt hammer including a plunger having a convex distal tip, wherein the Schmidt hammer is configured to impart an impact force on an anchor bolt embedded in concrete in registration with the convex distal tip and to record a rebound distance travelled by an impact mass,
    data analysis circuitry configured to determine a rebound number based on the rebound distance travelled by the impact mass;
    an ultrasonic pulse velocity tester having a transmitting transducer and a receiving transducer, wherein the transmitting transducer is configured to contact the concrete at a first location surrounding the anchor bolt and the receiving transducer is configured to contact the concrete at a second location surrounding the anchor bolt and spaced from the first location;
    circuitry configured to drive the transmitting transducer to send an ultrasonic pulse through the concrete at a first time, the circuitry further configured to receive an electrical signal generated by the receiving transducer based on the ultrasonic pulse at a second time, the circuitry including first processing circuitry configured to determine the transit time of the ultrasonic pulse through the concrete based on the difference between first time and the second time;
    a controller in communication with the Schmidt hammer, the data analysis circuitry and the ultrasonic pulse velocity tester, the controller having second processing circuitry configured to correlate a Schmidt hammer rebound number with the ultrasonic pulse transit time within the concrete to determine a pullout load capacity and the bond quality of the embedded anchor bolt;
    a digital level connected to the Schmidt hammer and including a magnet and a plurality of Hall effect sensors, wherein the Hall effect sensors generate signals based on the gravitational magnetic field and the magnetic field of the magnet, and
    a data analysis module including circuitry configured to receive the Hall effect signals from the digital level, calculate vertical and horizontal angles of inclination of the Schmidt hammer based on the Hall effect signals, and correct the rebound number based on the vertical and horizontal angles of inclination, and display the vertical and horizontal angles of inclination and the corrected rebound number on the display of the Schmidt hammer body.

2. The testing device of claim 1, wherein the Schmidt hammer body further comprises a guide tube having a distal end configured to contact the concrete surface, the guide tube further configured to support alignment of the plunger with the anchor bolt in order to alleviate slippage of the distal tip on the anchor bolt.

3. The system of claim 1, wherein the Schmidt hammer has a body having a central axis, a proximal end and a distal end coaxially located with the central axis; the Schmidt hammer further comprising:
    the impact mass disposed coaxial with and displaceable along the central axis from the proximal end towards the distal end to impact against the plunger;
    a drive mechanism for driving the impact mass along the central axis;
    a rebound detector to measure the rebound distance;
    a display;
    a transmitter; and
    a data acquisition module to receive the rebound distance,
    wherein the plunger is coaxially located along the axis, the plunger having a proximal end for receiving the impact from the impact mass.

4. The system of claim 3, wherein the data analysis has circuitry configured to display the rebound number and transmit the rebound number to the controller.

5. The system of claim 4, wherein the data analysis module including circuitry configured to display the vertical and horizontal angles of inclination and the corrected rebound number on the display of the Schmidt hammer body.

6. A non-destructive testing method for evaluating the pullout load capacity and bond quality for anchor bolts embedded in concrete, comprising:
    measuring a rebound number of an anchor bolt embedded in concrete by using a Schmidt hammer;
    transmitting the rebound number to a controller connected to the Schmidt hammer;
    measuring an ultrasonic pulse transit time in the concrete surrounding the anchor bolt by using an ultrasonic pulse velocity tester;
    measuring an angle of inclination of the plunger with a digital level connected to Schmidt hammer;
    correcting the rebound number based on the angle of inclination of the plunger;
    transmitting the corrected rebound number to the controller;
    estimating the pull out load carrying capacity of the installed anchor bolt by correlating the rebound number with the ultrasonic transit time; and
    evaluating the bond quality of the embedded anchor bolt with the concrete.

7. The non-destructive testing method of claim 6, wherein measuring a rebound number further comprises
    contacting, with a distal end of a guide tube, the concrete structure;
    contacting the embedded anchor bolt with the convex distal tip of the plunger;
    driving an impact mass along a central axis of the Schmidt hammer to impact the plunger;
    impacting the anchor bolt with the convex distal tip of the plunger;
    measuring the rebound distance of the mass; and generating a rebound number based on the rebound distance.

8. The non-destructive testing method of claim 6, wherein measuring an ultrasonic pulse transit time comprises
   contacting the concrete at a first location surrounding the anchor bolt with a transmitting transducer;
   contacting the concrete at a second location surrounding the anchor bolt and spaced from the first location with a receiving transducer;
   generating an ultrasonic pulse with the transmitting transducer at a first time;
   receiving the ultrasonic pulse with the receiving transducer at a second time later than the first time, the receiving transducer generating an electrical signal in response to receiving the ultrasonic pulse;
   calculating the ultrasonic pulse transit time by subtracting the first time from the second time;
   recording the ultrasonic pulse transit time in a memory of the ultrasonic pulse velocity tester; and
   displaying the ultrasonic pulse transit time on a display of the ultrasonic pulse velocity tester.

9. The non-destructive testing method of claim 8, further comprising
   transmitting the ultrasonic pulse transit time to a controller connected to the ultrasonic pulse velocity tester, wherein the controller is at least one of connected wirelessly to the ultrasonic pulse velocity tester and connected by wiring to the ultrasonic pulse velocity tester.

10. The non-destructive testing method of claim 9, wherein estimating the pull out load capacity of the embedded anchor bolt further comprises
   receiving the Schmidt hammer rebound number at the controller, wherein the controller includes a database, a memory, a processor, a transceiver and a receiver;
   retrieving, from data stored in the database, an embedment length, an anchor bolt diameter and a concrete strength;
   combining the Schmidt hammer rebound number, R, with the embedment length, Ld, anchor bolt diameter, Bd, and concrete strength, Cs, to generate a vector x, where x={R, Le, Bd, Cs};
   receiving the transit time, TT, from the ultrasonic pulse velocity tester at the controller;
   combining the transit time with the with the vector x to generate a vector y, where y={R, Le, Bd, Cs, TT};
   matching the vector y with a record from a look up table stored in the database, wherein the lookup table record relates the vector y to a pull out load capacity.

11. The non-destructive testing method of claim 9, wherein evaluating the bond quality of the embedded anchor bolt with the concrete structure comprises
   receiving the Schmidt hammer rebound number at the controller, wherein the controller includes a database, a memory, a processor, a transceiver and a receiver;
   retrieving, from data stored in the database, an embedment length, anchor bolt diameter and concrete strength;
   combining the Schmidt hammer rebound number, R, with the embedment length, Ld, anchor bolt diameter, Bd, and concrete strength, Cs, to generate a vector x, where x={R, Le, Bd, Cs};
   receiving the transit time, TT, at the controller, from the ultrasonic pulse velocity tester;
   comparing the transit time, TT, to ultrasonic pulse transit time thresholds stored in the database, the ultrasonic pulse transit time thresholds related to porosity, P, internal cracking, IC, air voids, AV, and water pockets, W, around the embedded anchor bolt;
   generating a vector z, where $z_i=\{TT, P_i, IC_i, AV_i, W_i\}$ and $P_i=1$ if $TT \geq P$ and $P_i=0$ if $TT \leq P$, $IC_i=1$ if $TT \geq IC$ and $IC_i=0$ if $TT \leq IC$, $AV_i=1$ if $TT \geq AV$ and $AV_i=0$ if $TT \leq AV$, and $P_i=1$ if $TT \geq P$ and $P_i=0$ if $TT \leq P$; where i is an integer;
   adding the vector z to the vector x to generate a vector k, where $k=\{R, Ld, Bd, Cs, TT, P_i, IC_i, AV_i, W_i\}$;
   matching the vector k with a record from a look up table stored in the database, wherein the lookup table record relates the values of the vector k to the bond quality of the embedded anchor bolt with the concrete structure.

12. The non-destructive testing method of claim 11, further comprising
   measuring the angle of inclination of the plunger with the digital level;
   correcting the rebound number based on the angle of inclination;
   displaying the corrected rebound number and the angle of inclination on a display of the Schmidt hammer;
   transmitting the corrected rebound number, Rc, to the controller;
   generating a vector $k_c$, where $k_c=\{R, Le, Bd, Cs, TT, P_i, IC_i, AV_i, W_i\}$;
   matching the vector $k_c$ with a record from a look up table stored in the database, wherein the lookup table record relates the values of the vector $k_c$ to the bond quality of the embedded anchor bolt with the concrete structure.

13. The method of claim 6, wherein the measuring the rebound number comprises:
   driving the impact mass along a central axis of the Schmidt hammer to impact a plunger;
   impacting the anchor bolt with a convex distal tip of the plunger;
   measuring the rebound distance of the mass; and
   generating the rebound number based on the rebound distance.

14. The method of claim 13, wherein the controller is at least one of connected wirelessly to the Schmidt hammer and connected by wiring to the Schmidt hammer.

15. The method of claim 14, further comprising:
   displaying the corrected rebound number and the angle of inclination on a display of the Schmidt hammer.

16. The method of claim 6, wherein the digital level is integrated into the Schmidt hammer.

\* \* \* \* \*